(12) United States Patent  
Casey et al.

(10) Patent No.: US 12,226,315 B2  
(45) Date of Patent: Feb. 18, 2025

(54) KINEMATIC DATA-BASED PATIENT-SPECIFIC ARTIFICIAL DISCS, IMPLANTS AND ASSOCIATED SYSTEMS AND METHODS

(71) Applicant: Carlsmed, Inc., La Jolla, CA (US)

(72) Inventors: Niall Patrick Casey, Carlsbad, CA (US); Jeffrey Roh, Seattle, WA (US)

(73) Assignee: Carlsmed, Inc., Carlsbad, CA (US)

( * ) Notice: Subject to any disclaimer, the term of this patent is extended or adjusted under 35 U.S.C. 154(b) by 1187 days.

(21) Appl. No.: 16/987,113

(22) Filed: Aug. 6, 2020

(65) Prior Publication Data

US 2022/0039965 A1     Feb. 10, 2022

(51) Int. Cl.
*A61F 2/30*     (2006.01)
*A61B 34/10*    (2016.01)

(52) U.S. Cl.
CPC .... *A61F 2/30942* (2013.01); *A61B 2034/104* (2016.02); *A61B 2034/105* (2016.02); *A61B 2034/108* (2016.02)

(58) Field of Classification Search
CPC ....... A61F 2/30942; A61F 2002/30948; A61B 2034/104; A61B 2034/105; A61B 2034/108; A61B 34/10
See application file for complete search history.

(56) References Cited

U.S. PATENT DOCUMENTS

| | | |
|---|---|---|
| 4,704,686 A | 11/1987 | Aldinger |
| 4,936,862 A | 6/1990 | Walker et al. |
| 5,431,562 A | 7/1995 | Andreiko et al. |
| D420,995 S | 2/2000 | Imamura |
| D436,580 S | 1/2001 | Navano |
| 6,315,553 B1 | 11/2001 | Sachdeva |
| 6,447,448 B1 * | 9/2002 | Ishikawa ................ A61B 5/036 600/377 |

(Continued)

FOREIGN PATENT DOCUMENTS

| | | |
|---|---|---|
| CN | 104318009 A | 1/2015 |
| CN | 104353121 A | 2/2015 |

(Continued)

OTHER PUBLICATIONS

Endo, Kenji et al. "Measurement of whole spine sagittal alignment using the SLOT radiography of the SONIALVISION safire series clinical application." Medical Now, No. 78; Aug. 2015, 4 pages.

(Continued)

*Primary Examiner* — Chun Cao
(74) *Attorney, Agent, or Firm* — Perkins Coie LLP

(57) ABSTRACT

Systems and methods for designing patient-specific medical devices are described herein. In some embodiments, a method includes obtaining patient data that includes image data and kinematic data of a patient's spine. A virtual model of the patient's spine is generated and can be manipulated until a target anatomical configuration is achieved. A patient-specific implant can then be designed based at least in part on the target anatomical configuration and the kinematics such that, when the patient-specific implant is implanted in the patient, the patient-specific implant provides the target anatomical correction while maintaining or improving the kinematics of the patient's spine.

40 Claims, 6 Drawing Sheets

(56) References Cited

U.S. PATENT DOCUMENTS

| | | |
|---|---|---|
| 6,540,512 B1 | 4/2003 | Sachdeva |
| 6,696,073 B2 | 2/2004 | Boyce et al. |
| 6,772,026 B2 | 8/2004 | Bradbury |
| 6,932,842 B1 | 8/2005 | Litschko et al. |
| 6,978,188 B1 | 12/2005 | Christensen |
| 6,988,241 B1 | 1/2006 | Guttman |
| 7,174,282 B2 | 2/2007 | Hollister et al. |
| 7,187,790 B2 | 3/2007 | Sabol et al. |
| D548,242 S | 8/2007 | Viegers |
| D614,191 S | 4/2010 | Takano |
| 7,747,305 B2 | 6/2010 | Dean et al. |
| 7,756,314 B2 | 7/2010 | Karau et al. |
| 7,799,077 B2 | 9/2010 | Lang |
| D633,514 S | 3/2011 | Tokunaga |
| D656,153 S | 3/2012 | Imamura |
| 8,246,680 B2 | 8/2012 | Betz |
| 8,265,949 B2 | 9/2012 | Haddad |
| 8,275,594 B2 | 9/2012 | Lin |
| 8,337,507 B2 | 12/2012 | Lang |
| 8,394,142 B2 | 3/2013 | Bertagnoli |
| 8,457,930 B2 | 6/2013 | Shroeder |
| 8,532,806 B1 | 9/2013 | Masson |
| 8,556,983 B2 | 10/2013 | Bojarski et al. |
| 8,644,568 B1 | 2/2014 | Hoffman |
| 8,735,773 B2 | 5/2014 | Lang |
| 8,758,357 B2 | 6/2014 | Frey |
| 8,775,133 B2 | 7/2014 | Schroeder |
| 8,781,557 B2 | 7/2014 | Dean |
| 8,843,229 B2 | 9/2014 | Vanasse |
| 8,855,389 B1 | 10/2014 | Hoffman |
| 8,870,889 B2 | 10/2014 | Frey |
| 9,020,788 B2 | 4/2015 | Lang |
| D735,231 S | 7/2015 | Omiya |
| D737,309 S | 8/2015 | Kito |
| 9,198,678 B2 | 12/2015 | Frey et al. |
| 9,208,558 B2 | 12/2015 | Dean |
| D757,025 S | 5/2016 | Kim |
| D761,842 S | 7/2016 | Johnson |
| 9,411,939 B2 | 8/2016 | Furrer |
| 9,445,907 B2 | 9/2016 | Meridew |
| 9,452,050 B2 | 9/2016 | Miles et al. |
| D774,076 S | 12/2016 | Fuller |
| 9,542,525 B2 | 1/2017 | Arisoy et al. |
| 9,642,633 B2 | 5/2017 | Frey et al. |
| 9,693,831 B2 | 7/2017 | Mosnier et al. |
| 9,707,058 B2 | 7/2017 | Bassett |
| 9,715,563 B1 | 7/2017 | Schroeder |
| D797,760 S | 9/2017 | Tsujimura |
| D797,766 S | 9/2017 | Ibsies |
| D798,312 S | 9/2017 | Tsujimura |
| 9,757,245 B2 | 9/2017 | O'Neil et al. |
| D798,894 S | 10/2017 | Ibsies |
| 9,775,680 B2 | 10/2017 | Bojarski et al. |
| 9,782,228 B2 | 10/2017 | Mosnier et al. |
| D812,628 S | 3/2018 | Okado |
| 9,993,341 B2 | 6/2018 | Vanasse |
| 10,034,676 B2 | 7/2018 | Donner |
| D825,605 S | 8/2018 | Jann |
| D826,977 S | 8/2018 | Nakajima |
| 10,089,413 B2 | 10/2018 | Wirx-Speetjens et al. |
| D841,675 S | 2/2019 | Hoffman |
| 10,213,311 B2 | 2/2019 | Mafhouz |
| D845,973 S | 4/2019 | Jaycobs |
| D845,974 S | 4/2019 | Cooperman |
| D847,165 S | 4/2019 | Kolbenheyer |
| D848,468 S | 5/2019 | Ng |
| D849,029 S | 5/2019 | Cooperman |
| D849,773 S | 5/2019 | Jiang |
| 10,292,770 B2 | 5/2019 | Ryan |
| 10,299,863 B2 | 5/2019 | Grbic et al. |
| D854,560 S | 7/2019 | Field |
| D854,561 S | 7/2019 | Field |
| 10,390,958 B2 | 8/2019 | Maclennan |
| D860,237 S | 9/2019 | Li |
| D860,238 S | 9/2019 | Bhardwaj |
| D866,577 S | 11/2019 | Eisert |
| D867,379 S | 11/2019 | Ang |
| D867,389 S | 11/2019 | Jamison |
| 10,463,433 B2 | 11/2019 | Turner et al. |
| D870,762 S | 12/2019 | Mendoza |
| 10,512,546 B2 | 12/2019 | Kamer et al. |
| 10,517,681 B2 | 12/2019 | Roh et al. |
| D872,117 S | 1/2020 | Kobayashi |
| D872,756 S | 1/2020 | Howell |
| D874,490 S | 2/2020 | Dodsworth |
| D875,761 S | 2/2020 | Heffernan |
| D876,454 S | 2/2020 | Knowles |
| D876,462 S | 2/2020 | Li |
| D877,167 S | 3/2020 | Knowles |
| D879,112 S | 3/2020 | Hejazi |
| 10,588,589 B2 | 3/2020 | Bregman-Amitai et al. |
| 10,603,055 B2 | 3/2020 | Donner et al. |
| D880,513 S | 4/2020 | Wang |
| D881,908 S | 4/2020 | Sunil |
| D881,910 S | 4/2020 | Lin |
| 10,621,289 B2 | 4/2020 | Schroeder |
| 10,631,988 B2 | 4/2020 | Arnold et al. |
| D884,008 S | 5/2020 | Thornberg |
| 10,646,236 B2 | 5/2020 | Donner et al. |
| 10,646,258 B2 | 5/2020 | Donner et al. |
| 10,736,698 B2 | 8/2020 | Bohl |
| 10,751,188 B2 | 8/2020 | Guo et al. |
| D896,825 S | 9/2020 | Abel |
| D896,828 S | 9/2020 | Linares |
| D898,054 S | 10/2020 | Everhart |
| D899,438 S | 10/2020 | Crafts |
| 10,806,597 B2 | 10/2020 | Sournac et al. |
| 10,902,944 B1 | 1/2021 | Casey et al. |
| D916,868 S | 4/2021 | Evangeliou |
| D916,879 S | 4/2021 | Mitsumori |
| D918,253 S | 5/2021 | Choe |
| 11,000,334 B1 | 5/2021 | Young |
| D921,675 S | 6/2021 | Kmak |
| D921,677 S | 6/2021 | Kmak |
| D921,687 S | 6/2021 | Kmak |
| D924,909 S | 7/2021 | Nasu |
| D925,567 S | 7/2021 | Hayamizu |
| D927,528 S | 8/2021 | Heisler |
| 11,083,586 B2 | 8/2021 | Cordonnier |
| D933,692 S | 10/2021 | Smith |
| D937,870 S | 12/2021 | Pinto |
| D937,876 S | 12/2021 | Harvey |
| D938,461 S | 12/2021 | Hoffman |
| D938,986 S | 12/2021 | Grossberg |
| D940,178 S | 1/2022 | Ang |
| D946,022 S | 3/2022 | Nuttbrown |
| D946,023 S | 3/2022 | Nuttbrown |
| D946,024 S | 3/2022 | Vogler-Ivashchanka |
| D946,616 S | 3/2022 | Tsai |
| D958,151 S | 7/2022 | Casey et al. |
| 2002/0007294 A1 | 1/2002 | Bradbury et al. |
| 2004/0104512 A1 | 6/2004 | Eidenschink |
| 2004/0171924 A1 | 9/2004 | Mire et al. |
| 2005/0049590 A1 | 3/2005 | Alleyne et al. |
| 2005/0271996 A1 | 12/2005 | Sporbert et al. |
| 2006/0009780 A1 | 1/2006 | Foley |
| 2007/0118243 A1 | 5/2007 | Schroeder |
| 2007/0276501 A1* | 11/2007 | Betz .............. A61F 2/30942 264/222 |
| 2008/0089566 A1* | 4/2008 | Node-Langlois ......... G06T 7/30 382/128 |
| 2008/0161680 A1 | 7/2008 | von Jako |
| 2008/0195240 A1 | 8/2008 | Martin |
| 2008/0227047 A1 | 9/2008 | Lowe |
| 2009/0062739 A1 | 3/2009 | Anderson |
| 2010/0191088 A1 | 7/2010 | Anderson |
| 2010/0292963 A1 | 11/2010 | Schroeder |
| 2010/0324692 A1 | 12/2010 | Uthgenannt |
| 2011/0218545 A1 | 9/2011 | Catanzarite et al. |
| 2011/0301710 A1 | 12/2011 | Mather et al. |
| 2012/0010710 A1 | 1/2012 | Frigg |
| 2012/0084064 A1 | 4/2012 | Dzenis et al. |
| 2012/0116203 A1 | 5/2012 | Vancraen |
| 2012/0150243 A9 | 6/2012 | Crawford |

(56) References Cited

U.S. PATENT DOCUMENTS

| | | |
|---|---|---|
| 2012/0191192 A1 | 7/2012 | Park |
| 2012/0287238 A1 | 11/2012 | Onishi |
| 2012/0296433 A1 | 11/2012 | Farin |
| 2012/0322018 A1 | 12/2012 | Lowe |
| 2013/0211531 A1 | 8/2013 | Steines et al. |
| 2013/0323669 A1 | 12/2013 | Lowe |
| 2014/0072608 A1 | 3/2014 | Karagkiozaki |
| 2014/0074438 A1 | 3/2014 | Furrer |
| 2014/0081659 A1 | 3/2014 | Nawana et al. |
| 2014/0086780 A1 | 3/2014 | Miller |
| 2014/0100886 A1 | 4/2014 | Woods |
| 2014/0142703 A1 | 5/2014 | Hansell et al. |
| 2014/0164022 A1 | 6/2014 | Reed |
| 2014/0263674 A1 | 9/2014 | Cerveny |
| 2014/0350614 A1 | 11/2014 | Frey |
| 2015/0079533 A1 | 3/2015 | Lowe |
| 2015/0105891 A1 | 4/2015 | Golway et al. |
| 2015/0199488 A1 | 7/2015 | Falchuk |
| 2015/0213225 A1 | 7/2015 | Amarasingham |
| 2015/0324490 A1 | 11/2015 | Page |
| 2015/0328004 A1 | 11/2015 | Mafhouz |
| 2015/0332018 A1 | 11/2015 | Rosen |
| 2016/0001039 A1 | 1/2016 | Armour et al. |
| 2016/0015465 A1 | 1/2016 | Steines et al. |
| 2016/0030067 A1 | 2/2016 | Frey et al. |
| 2016/0074048 A1 | 3/2016 | Pavlovskaia |
| 2016/0117817 A1 | 4/2016 | Seel |
| 2016/0143744 A1 | 5/2016 | Bojarski et al. |
| 2016/0184054 A1 | 6/2016 | Lowe |
| 2016/0210374 A1 | 7/2016 | Mosnier et al. |
| 2016/0217268 A1 | 7/2016 | Otto |
| 2016/0242857 A1 | 8/2016 | Scholl |
| 2016/0300026 A1 | 10/2016 | Bogoni et al. |
| 2016/0317309 A1* | 11/2016 | Al Hares ............ A61F 2/30942 |
| 2016/0354039 A1 | 12/2016 | Soto et al. |
| 2016/0378919 A1 | 12/2016 | McNutt et al. |
| 2017/0000566 A1 | 1/2017 | Gordon |
| 2017/0014169 A1 | 1/2017 | Dean |
| 2017/0020679 A1 | 1/2017 | Maclennan |
| 2017/0035514 A1 | 2/2017 | Fox et al. |
| 2017/0061375 A1 | 3/2017 | Laster |
| 2017/0068792 A1 | 3/2017 | Reiner |
| 2017/0135706 A1 | 5/2017 | Frey et al. |
| 2017/0143494 A1 | 5/2017 | Mahfouz |
| 2017/0143831 A1 | 5/2017 | Varanasi et al. |
| 2017/0216047 A1 | 8/2017 | Hawkes et al. |
| 2017/0220740 A1 | 8/2017 | D'Urso |
| 2017/0252107 A1 | 9/2017 | Turner et al. |
| 2017/0262595 A1 | 9/2017 | Vorhis |
| 2017/0340447 A1 | 11/2017 | Mahfouz |
| 2017/0354510 A1 | 12/2017 | O'Neil et al. |
| 2017/0367645 A1 | 12/2017 | Klinder |
| 2018/0008349 A1 | 1/2018 | Gillman |
| 2018/0055644 A1 | 3/2018 | Mahfouz |
| 2018/0113992 A1 | 4/2018 | Eltorai et al. |
| 2018/0116727 A1 | 5/2018 | Caldwell et al. |
| 2018/0168499 A1 | 6/2018 | Bergold |
| 2018/0168731 A1 | 6/2018 | Reid |
| 2018/0185075 A1 | 7/2018 | She |
| 2018/0228614 A1 | 8/2018 | Lang et al. |
| 2018/0233222 A1 | 8/2018 | Daley |
| 2018/0233225 A1 | 8/2018 | Experton |
| 2018/0250075 A1 | 9/2018 | Cho |
| 2018/0303552 A1 | 10/2018 | Ryan |
| 2018/0303616 A1 | 10/2018 | Bhattacharyya et al. |
| 2018/0308569 A1 | 10/2018 | Luellen |
| 2018/0338841 A1 | 11/2018 | Miller et al. |
| 2019/0029757 A1 | 1/2019 | Roh et al. |
| 2019/0065685 A1 | 2/2019 | Pickover |
| 2019/0146458 A1 | 5/2019 | Roh et al. |
| 2019/0156482 A1 | 5/2019 | Deitz et al. |
| 2019/0201106 A1 | 7/2019 | Siemionow |
| 2019/0262084 A1 | 8/2019 | Roh et al. |
| 2019/0266597 A1 | 8/2019 | Mohtar |
| 2019/0282367 A1 | 9/2019 | Casey et al. |
| 2019/0321193 A1 | 10/2019 | Casey et al. |
| 2019/0328929 A1 | 10/2019 | Kugler et al. |
| 2019/0333622 A1 | 10/2019 | Levin |
| 2019/0354693 A1 | 11/2019 | Yoon |
| 2019/0380782 A1 | 12/2019 | McAffee et al. |
| 2019/0380792 A1 | 12/2019 | Poltaretskyi et al. |
| 2020/0021570 A1 | 1/2020 | Lin |
| 2020/0078180 A1 | 3/2020 | Casey et al. |
| 2020/0085509 A1 | 3/2020 | Roh et al. |
| 2020/0093542 A1 | 3/2020 | Arramon et al. |
| 2020/0170802 A1* | 6/2020 | Casey ................. A61F 2/30942 |
| 2020/0197107 A1 | 6/2020 | Ryan et al. |
| 2020/0261156 A1 | 8/2020 | Schmidt |
| 2020/0289288 A1 | 9/2020 | Müller et al. |
| 2020/0315708 A1 | 10/2020 | Mosnier et al. |
| 2021/0059822 A1 | 3/2021 | Casey et al. |
| 2021/0064605 A1 | 3/2021 | Balint |
| 2021/0145519 A1 | 5/2021 | Mosnier et al. |
| 2021/0192759 A1* | 6/2021 | Lang ..................... A61B 34/20 |
| 2021/0210189 A1 | 7/2021 | Casey et al. |
| 2021/0287770 A1 | 9/2021 | Anderson |
| 2021/0382457 A1 | 12/2021 | Roh et al. |
| 2022/0000556 A1 | 1/2022 | Casey et al. |
| 2022/0000625 A1 | 1/2022 | Cordonnier |
| 2022/0006642 A1 | 1/2022 | Maj et al. |
| 2022/0047402 A1 | 2/2022 | Casey et al. |
| 2022/0110686 A1 | 4/2022 | Roh et al. |
| 2022/0160405 A1 | 5/2022 | Casey et al. |
| 2022/0160518 A1 | 5/2022 | Casey et al. |

FOREIGN PATENT DOCUMENTS

| | | |
|---|---|---|
| CN | 204468348 U | 7/2015 |
| CN | 105796214 A | 7/2016 |
| CN | 106202861 | 12/2016 |
| CN | 107220933 | 9/2017 |
| CN | 108670506 A | 10/2018 |
| CN | 110575289 A | 12/2019 |
| CN | 111281613 A | 6/2020 |
| CN | 112155792 A | 1/2021 |
| CN | 113643790 | 11/2021 |
| EP | 3120796 A1 | 1/2017 |
| WO | 9507509 | 3/1995 |
| WO | 2004110309 A2 | 12/2004 |
| WO | 2010151564 A1 | 12/2010 |
| WO | 2012154534 | 11/2012 |
| WO | 2014180972 A2 | 11/2014 |
| WO | 2016172694 A1 | 10/2016 |
| WO | 2019112917 A1 | 6/2019 |
| WO | 2019148154 A1 | 8/2019 |
| WO | 2022045956 | 3/2022 |

OTHER PUBLICATIONS

International Search Report and Written Opinion for International Application No. PCT/US19/50885, mailed Jan. 28, 2020 (21 pages).

International Search Report and Written Opinion for International Application No. PCT/US19/63855, mailed Feb. 14, 2020 (15 pages).

International Searching Authority, International Search Report and Written Opinion, PCT Patent Application PCT/US2018/063530, mailed Feb. 12, 2019, 16 pages.

International Search Report and Written Opinion for International Patent Application No. PCT/US21/12065, mailed Apr. 29, 2021 (19 pages).

Materialise Mimics, "Efficiently turn scans into accurate virtual 3D models," <www.materialize.com/en/medical/software/mimics>, 1 page.

Pimenta, Dr. Luiz, "Current Surgical Strategies to Restore Proper Sagittal Alignment," Journal of Spine 2015, vol. 4, Issue 4, 2 pages.

U.S. Appl. No. 15/958,409 for Ryan, filed Apr. 21, 2017.

International Search Report and Written Opinion for International Application No. PCT/US2248729, mailed Feb. 17, 2023, 18 pages.

Extended European Search Report for European Application No. 18885367.5, mailed Aug. 16, 2021, 8 pages.

International Search Report and Written Opinion for International Application No. PCT/US21/44878, mailed Nov. 16, 2021, 18 pages.

(56) References Cited

OTHER PUBLICATIONS

International Search Report and Written Opinion for International Application No. PCT/US21/45503, mailed Jan. 11, 2022, 19 pages.
International Search Report and Written Opinion for International Patent Application No. PCT/US21/59837, mailed Feb. 7, 2022, 19 pages.
Majdouline et al., "Preoperative assessment and evaluation of instrumentation strategies for the treatment of adolescent idiopathic scoliosis: computer simulation and optimization." Scoliosis 7, 21 (2012), pp. 1-8.
Eshkalak, S.K. et al., "The role of three-dimensional printing in healthcare and medicine." Materials and Design 194, Jul. 10, 20202, 15 pages.
Extended European Search Report for European Application No. 19859930.0, mailed Jun. 22, 2022, 7 pages.
International Search Report and Written Opinion for International Patent Application No. PCT/US21/60074, mailed Mar. 17, 2022, 21 pages.
Pruthi, G. et al., "Comprehensive review of guidelines to practice prosthodontic and implant procedures during COVID-19 pandemic." Journal of Oral Biology and Craniofacial Research 10, Oct. 17, 2020, 8 pages.
U.S. Appl. No. 17/518,524 for Cordonnier, filed Nov. 3, 2021.

\* cited by examiner

KINEMATIC DATA-BASED PATIENT-SPECIFIC ARTIFICIAL DISCS, IMPLANTS AND ASSOCIATED SYSTEMS AND METHODS

TECHNICAL FIELD

The present disclosure is generally related to orthopedic implants, and more particularly to systems and methods for designing and implementing patient-specific orthopedic implants.

BACKGROUND

Orthopedic implants are used to correct numerous different maladies in a variety of contexts, including spine surgery, hand surgery, shoulder and elbow surgery, total joint reconstruction (arthroplasty), skull reconstruction, pediatric orthopedics, foot and ankle surgery, musculoskeletal oncology, surgical sports medicine, and orthopedic trauma. Spine surgery itself may encompass a variety of procedures and targets, such as one or more of the cervical spine, thoracic spine, lumbar spine, or sacrum, and may be performed to treat a deformity or degeneration of the spine and/or related back pain, leg pain, or other body pain. Common spinal deformities that may be treated using an orthopedic implant include irregular spinal curvature such as scoliosis, lordosis, or kyphosis (hyper- or hypo-), and irregular spinal displacement (e.g., spondylolisthesis). Other spinal disorders that can be treated using an orthopedic implant include osteoarthritis, lumbar degenerative disc disease or cervical degenerative disc disease, lumbar spinal stenosis, and cervical spinal stenosis.

In some instances, orthopedic implants (e.g., artificial discs) are implanted into a patient's spine to restore alignment of the spine while retaining the mobility of the spine. Disc replacement procedures may be performed on lumbar, thoracic, and cervical discs. Artificial cervical, thoracic, and lumbar discs may be surgically implanted to improve disc height, alignment, or mobility. For example, artificial discs can be used to improve or restore the relative position of vertebrae, establish appropriate foraminal height, decompress nerves, and provide relative motion between spinal segments. Unlike with conventional implants used in spinal fusion surgery, artificial discs imitate the functions of the patient's native disc, enabling adjacent vertebrae to "move" relative to one another to preserve a natural range of motion. To implant an artificial disc into a patient's spine, a physician may remove some or the entirety of the patient's degenerating native disc tissue. The physician may then insert an artificial disc in place of the removed native disc tissue and secure it to the vertebrae using known techniques.

BRIEF DESCRIPTION OF THE DRAWINGS

The accompanying drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Non-limiting and non-exhaustive descriptions are described with reference to the following drawings. The components in the figures are not necessarily to scale, emphasis instead being placed upon illustrating principles.

DETAILED DESCRIPTION

Overview of Technology

Figure 1A:
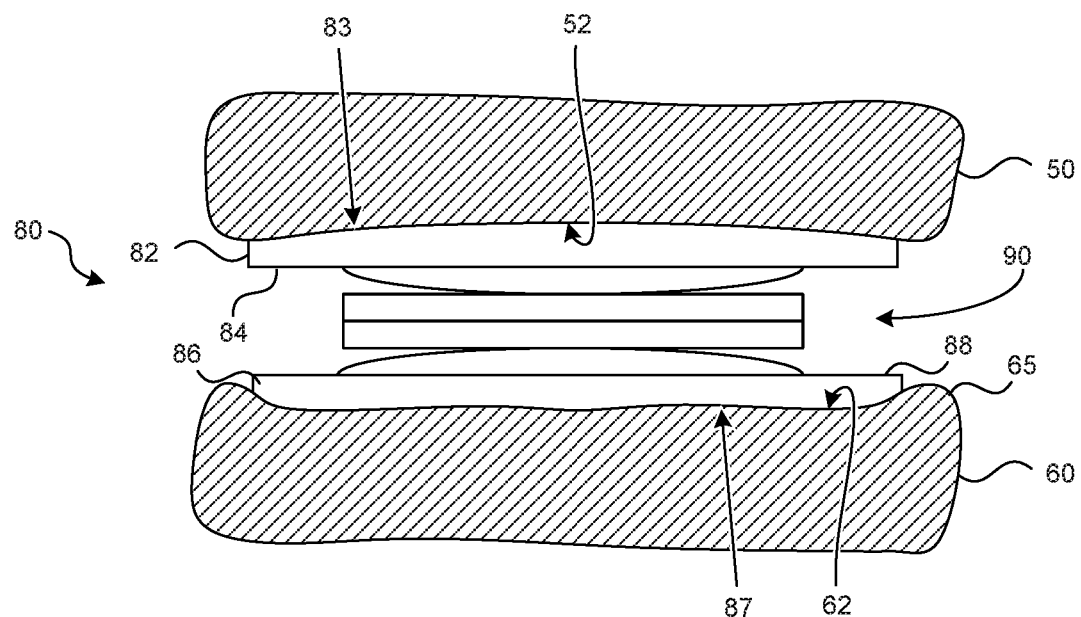
FIG. 1A is a schematic illustration of a patient-specific spinal implant positioned between vertebral bodies and in a first configuration in accordance with select embodiments of the present technology.

The present technology is directed to patient-specific medical device implants. For example, in many of the embodiments disclosed herein, the present technology provides systems and methods for designing, manufacturing, and/or providing patient-specific artificial discs (e.g., disc replacement devices, disc prostheses, spine arthroplasty devices, etc.) for use during a disc replacement surgery. The patient-specific artificial discs described herein can be specifically tailored to achieve one or more desired patient outcomes following implantation of the patient-specific artificial disc into the patient. For example, the patient-specific artificial discs can be sized and shaped to provide a correction to the patient's anatomy while also maintaining or improving patient kinematics. Accordingly, in some embodiments the patient-specific artificial discs can improve or restore a relative position of adjacent vertebrae while also permitting a desired range of motion between the adjacent vertebrae. Furthermore, the patient-specific artificial discs can have design characteristics (e.g., shape, topography, etc.) configured to mate with the particular patient's anatomy to reduce the risk of migration and further improve patient outcomes.

In some embodiments, the patient-specific artificial implants described herein are designed using patient data to enhance performance of the implant. The patient data can include image data (e.g., anatomy data), kinematic data (e.g., motion data), medical history, patient information, and the like. The anatomy data can include the geometry and/or topography of anatomical features, spacing between adjacent anatomical features, characteristics (e.g., tissue characteristics), and the like. The kinematic data can include range of motion data (e.g., target range of motion data, pre-surgery range of motion data, etc.) and other kinematic characteristics. The kinematic data can be collected by performing motion studies, modeling motion of joints using a software module, or other techniques. The kinematic data can be associated with a subject joint or motion segment.

In some embodiments, the patient-specific artificial implants described herein are designed using one or more design criteria, in addition to or in lieu of the patient data. The design criteria can include, but is not limited to, a target range of motion, a target vertebral spacing (e.g., minimum vertebral body spacing), vertebral endplate topography, implantation procedures (e.g., access path or procedure), expected service life, patient specific needs, regulatory requirements, etc. For example, the patient-specific artificial disc can be configured to match the intervertebral space, topology of vertebral endplates, kinematics of subject joints, or combinations thereof. In some procedures, the patient-specific artificial disc can be configured to maintain motion of the spine to reduce the risk of complications. In other procedures, the patient-specific artificial disc can be configured to increase motion of the spine. In some embodiments, the present technology incorporates predictive analytics, machine learning, neural networks, and/or artificial intelligence (AI) to define improved or optimal surgical interventions and/or implant designs in order to achieve the desired efficacy. For example, the patient data can be used to generate a patient-specific artificial disc design for providing one or more joint characteristics (e.g., range of motion, disc height, etc.).

In some embodiments, the present technology provides methods for providing patient-specific implants. In a particular embodiment, the method includes obtaining image data of one or more regions of a patient's spine that depicts a native anatomical configuration of the one or more regions. The method further includes obtaining kinematic data associated with the one or more regions of the patient's spine. The kinematic data can include values for one or more kinematic parameters, such as range of motion, angle of bend, angle of rotation, displacement, flexion, extension, flexion/extension arc, lateral bending, left/right bending arc, and/or axial rotation. The method further includes determining a target anatomical configuration different than the native anatomical configuration. A patient-specific implant is then designed based on the target anatomical configuration and the kinematic parameter values. In particular, the patient-specific implant is designed such that, when it is implanted in the patient, the patient-specific implant provides the target anatomical configuration while maintaining or improving the kinematic parameters.

In another particular embodiment, a computer-implemented method in accordance with the present technology includes receiving image data of one or more regions of a patient's spine that depicts a native anatomical configuration of the one or more regions. The method further includes measuring one or more kinematic parameters associated with the one or more regions and determining a target anatomical configuration different than the native anatomical configuration. A patient-specific implant is then designed based on the target anatomical configuration and the measured kinematic parameters. In particular, the patient-specific implant is designed such that, when it is implanted in the patient, the patient-specific implant provides the target anatomical configuration.

In some embodiments, a computer-implemented method for designing a patient-specific implant uses acquired patient data. The patient data can include one or more images, kinematic data, physician inputted data, or the like. The images can show native anatomical features of the patient. The kinematic data can be associated with the one or more regions and can include one or more specific values for various kinematic parameters. The kinematic parameters can include range of motion, angle of bend, angle of rotation, flexion/extension arcs, left/right bending arcs, lateral bending, displacement, and other parameters related to flexion, extension, bending, axial rotation, etc., and under a variety of conditions (e.g., load bearing, non-load bearing, etc.). The values for kinematic parameters can be determined based on images of the patient in different positions, measuring body position/motion, or the like. In some embodiments, the values for the kinematic parameters can be compared to target values for the kinematic parameters. The target values can be a target range of motion, angle of bend, angle of rotation, displacement, and/or other parameters related to flexion, extension, bending, axial rotation, or the like. A target anatomical configuration for one or more regions of the patient can also be determined. The target anatomical configuration can include an adjustment to one or more anatomical features relative to the native anatomical configuration, including, but not limited to, and adjustment to spacing between vertebral bodies, orientation of vertebral bodies, alignment of two or more vertebral bodies, lumbar lordosis, Cobb angle(s), pelvic incidence, disc height, segment flexibility, rotational displacement, and the like. At least a portion of the patient-specific implant can be designed based at least in part on the target anatomical configuration and the kinematic parameter values.

The computer-implemented method can include identification of anatomical features that impair body motion. The computer-implemented method can generate kinematic algorithms based on the identified features and can design the implant based on the kinematic algorithms to maintain a threshold amount of body motion, maintain pre-treatment body motion, and/or improve body motion. In some embodiments, a predicted amount of motion can be determined using one or more predictive models. A designer can update the predictive models. Secondary procedures can be performed on the identified anatomical features (e.g., stenosis, enlarged facet joints, bony overgrowths, loss of cartilage, etc.) to further enhance or affect body motion. The kinematic algorithms can model one or more segment of the spine as kinematic chain of links using constraints and boundary conditions to model segment configuration, movements, range of motion, degrees of freedom, etc. For example, a fixed link can represent fused vertebrae along the segment. Images of the patient's body in different positions and other patient data (including the present patient and/or prior patients) can be used to automatically generate a virtual model for two- or three-dimensional analysis.

The patient-specific artificial discs described herein are expected to provide a number of advantages over conventional artificial discs. For example, the patient-specific artificial discs described herein can reduce the number of surgical steps required during an implant procedure. Conventional spinal implants, including artificial disc implants, are manufactured in standard shapes and sizes and with standard flexibilities. Minimal consideration is paid to implant size and other characteristics before an implant procedure. Instead, during an implant procedure and with a patient's spine exposed, a surgeon will select a specific implant from a surgical kit containing a variety of sizes and shapes. Typically, the surgeon selects the implant size through a technique known as "trialing," during which the surgeon uses a series of incrementally sized implant proxies or subcomponents to determine the appropriate implant size and shape. Trialing can be a timely process, and the surgeon typically only focuses on the posterior height and sagittal angle of the implants, while largely ignoring the lateral heights and coronal angle of the implants. Using the present technology, the trailing process can be eliminated because the patient-specific artificial discs described herein have already been properly sized for the patient.

In addition, the patient-specific artificial discs can eliminate the need for surgical kits with arrays of different sized implants. As noted above, surgeons select conventional implants during operation from a stock or kit of implants. These kits require shipment and delivery of sufficient implants to cover the wide variety of patients and their unique interbody spaces. The shipping, sterilization, processing, and delivery of enough implants to the operating room for a single surgery is logistically burdensome and expensive. For example, it is not uncommon for more than fifty implants to be delivered to a surgery that requires only one implant. In addition to the logistical burden presented by these kits, the implant that is ultimately selected by the surgeon is still limited to the implants available in the surgical kit in the operating room. By selecting stock implants intraoperatively from a fixed assortment of implant sizes, the surgeon is therefore unable to provide the patient an optimal solution for correction of the particular spinal deformity or pathological malalignment causing the patient pain. Using the present technology, the need for surgical kits with a large number implants can be eliminated because the patient-specific artificial implant is specifically designed to fit the patient.

The patient-specific artificial discs can further facilitate proper placement and be designed to reduce the number of implant failures by optimizing fit, mobility, flexibility, and/or other characteristics of the implant. Improper placement or sizing of spinal implants can result in implant failures. For example, if an artificial disc is improperly placed, it can lead to issues with other joints of the motion segment. In one instance, if an artificial disc is not placed in the appropriate location or sized correctly, the associated facet joints can become over-stressed and suffer degeneration. Moreover, insufficient contact and load transfer between the vertebrae and the implant can produce inadequate fixation between the implant and anatomy. Inadequate fixation can allow the implant to move relative to the vertebrae, which can lead to improper placement of the implant. Furthermore, insufficient contact area or fixation between the interbody implant and the vertebrae can result in micro- and/or macro-motions that can reduce the opportunity for bone growth and fusion to the implant to occur. If enough motion occurs, expulsion of the interbody implant or subsidence of the interbody implant into the adjacent vertebrae can result. The patient-specific artificial discs described herein can therefore be configured to facilitate placement to limit stresses (e.g., limit stresses in the vertebral body, facet joints, etc.), enhance fixation, provide a relatively large contact area, or other design criteria. As one skilled in the art will appreciate from the disclosure herein, the patient-specific artificial implants may provide additional advantages over conventional implants and implant procedures, regardless of whether such problems are described herein.

The present technology thus provides systems and methods for designing "patient-specific" or "personalized" medical devices, such as artificial discs, that are expected to mitigate at least some of the foregoing disadvantages of conventional stock implants. In particular, the present technology provides systems and methods for designing patient-specific implants that are optimized for the patient's particular characteristics (e.g., condition, anatomy, pathology, medical history, etc.). For example, the patient-specific medical device can be designed and manufactured specifically for the particular patient, rather than being an off-the-shelf device. However, it shall be appreciated that a patient-specific or personalized medical device can include one or more components that are non-patient-specific, and/or can be used with an instrument or tool that is non-patient-specific. Personalized implant designs can be used to manufacture or select patient-specific technologies, including medical devices, instruments, and/or surgical kits. For example, a personalized surgical kit can include one or more patient-specific devices, patient-specific instruments, non-patient-specific technology (e.g., standard instruments, devices, etc.), instructions for use, patient-specific treatment plan information, or a combination thereof.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

As used herein and in the appended claims, the singular forms "a," "an," and "the" include plural references unless the context clearly dictates otherwise.

Although the disclosure herein primarily describes systems and methods for treatment planning in the context of orthopedic surgery, the technology may be applied equally to medical treatment and devices in other fields (e.g., other types of surgical practice). Additionally, although many embodiments herein describe systems and methods with respect to implanted devices, the technology may be applied equally to other types of medical devices (e.g., non-implanted devices).

Patient-Specific Implants

FIG. 1A is a schematic illustration of an exemplary patient-specific artificial disc implant 80 (referred to as "implant 80") positioned between vertebral bodies 50, 60 (shown in cross section). The implant 80 includes a first (e.g., upper) endplate 82 and a second (e.g., lower) endplate 86. The first endplate 82 can have an outer facing surface 83 and an inner facing surface 84. Likewise, the second endplate 86 can have an outer facing surface 87 and an inner facing surface 88. The implant 80 also includes a core 90 (e.g., nucleus) positioned between the first endplate 82 and the second endplate 86 (e.g., extending between and coupled to the inner surface 84 of the first endplate 82 and the inner surface 88 of the second endplate 86).

When the implant 80 is implanted in a patient, the outer surface 83 of the first endplate 82 engages with a lower (e.g., inferior) surface 52 of the first vertebral body 50, and the outer surface 87 of the second endplate 86 engages with an upper (e.g., superior) surface 62 of the second vertebral body 60 that is inferior/caudal to the first vertebral body 50. In some embodiments, the outer surface 83 of the first endplate 82 has a topology specifically tailored to mate with the topology of the surface 52 of the first vertebral body 50, and the outer surface 87 of the second endplate 86 has a topology specifically tailored to mate with the topology of the surface 62 of the second vertebral body 60. As used herein, the term "mate" can refer to the engagement of two surfaces with reduced and/or minimized empty space therebetween. For example, the outer surface 83 of the first endplate 82 can form a gapless or generally gapless interface with the surface 52 of the first vertebral body 50, and the outer surface 87 of the second endplate 86 can form a gapless or generally gapless interface with the surface 62 of the second vertebral body 60. The shape of the first endplate 82 and the second endplate 86 can therefore be designed based on the topology, shape, and features (e.g., ring apophysis, cortical rim, etc.) of the vertebral bodies with which they will interact once implanted. In the illustrated embodiment, for example, the periphery of the second endplate 86 is contoured to match the curvature of the ring apophysis 65 while the central region of first endplate 82 is generally convex to match the concavity of the central region of the first vertebral body 50. This provides a relatively large contact area to limit stresses in the first vertebral body 50 and the second vertebral body 60, facilitates seating of the implant 80, and/or limits or inhibits migration of the implant 80. Accordingly, in some embodiments the first endplate 82 and the second endplate 86 have different geometries and/or topographies to accommodate the different geometries and/or topographies of the first and second vertebral bodies. Without being bound by theory, improving the fit between the endplates and the vertebrae is expected to prevent and/or reduce instances of dynamic failure of the implants (e.g., by reducing and/or preventing micro-motions of the implant), and/or increase the efficacy of the implants.

Figure 1B:
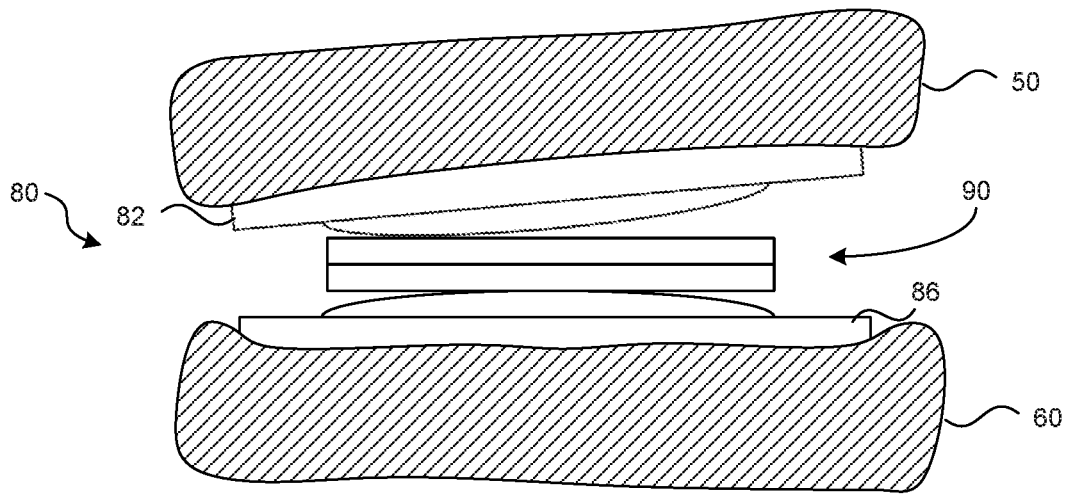
FIG. 1B is a schematic illustration of the spinal implant of FIG. 1A in a second configuration.

As best shown in FIG. 1B, the core 90 permits the first endplate 82 and/or the second endplate 86 to pivot or otherwise rotate relative to one another to accommodate motion between the first vertebral body 50 and the second vertebral body 60. Accordingly, the core 90 can also be referred to as a "motion segment." As described in greater detail below with respect to FIGS. 4 and 5, the core 90 can be designed to have the appropriate orientation, rotation, flexion, and/or translation to enable the first vertebral body 50 to move relative to the second vertebral body 60 in accordance with one or more target kinematic parameters. The degree and type of motion permitted by the core 90 can be based on a number of factors, including, but not limited to, the composition of the core, an interface between mated surfaces, and/or the geometry of the core (e.g., contour, shape, diameter, etc.). The core 90 can be made of any suitable materials including, but are not limited to, elastomeric polymers, rigid polymers, hybrid materials with elastomeric and rigid properties, ceramics, metals, and combinations thereof. The core 90 can also be comprised of a plurality of mating surfaces that provide the determined kinematics. For example, the core 90 can be a ball and socket type joint, dome and cup joint, etc. As another example, the core 90 can include one or more biasing members, springs, sliding members/interfaces, or other elastic feature(s). As one skilled in the art will appreciate, in some embodiments the core 90 can be omitted and the first endplate 82 and/or the second endplate 86 can be configured to provide motion in the implant 80. For example, the first endplate 82 may form an interface (e.g., an articulating interface) with the second endplate 86 that at least partially defines a motion segment in the implant. In such embodiments, the interface between the first endplate 82 and the second endplate 86 may be any suitable interface that permits movement between two components, including, but not limited to, a ball and socket interface, a dome and cup interface, a sliding interface, a rotating interface, etc. In some embodiments, the inner surface 84 of the first endplate 82 directly engages the inner surface 88 of the second endplate 86 to form the interface that defines the motion segment.

In some embodiments, the motion segment (e.g., the core 90 or an interface between the first endplate 82 and the second endplate 86) can include one or more patient-specific features to provide patient-specific kinematics. The patient-specific features can be selected based on the desired kinematics (e.g., degrees of freedom, type of motion, etc.) and can include type of joint, number of core members/layers, interface characteristics (e.g., between core members/layers), contours of mated surfaces, restriction elements (e.g., restriction pillars), etc. As described in detail below, patient data can be analyzed to configure the selected patient-specific features for a desired kinematics. If the desired range of motion is not achieved, additional or alternative patient-specific features can be selected until a target kinematics (e.g., range of motion, type of motion, etc.) is achieved. Accordingly, different components of the implant 80 can be designed based on different selected design criteria.

Figure 1C:
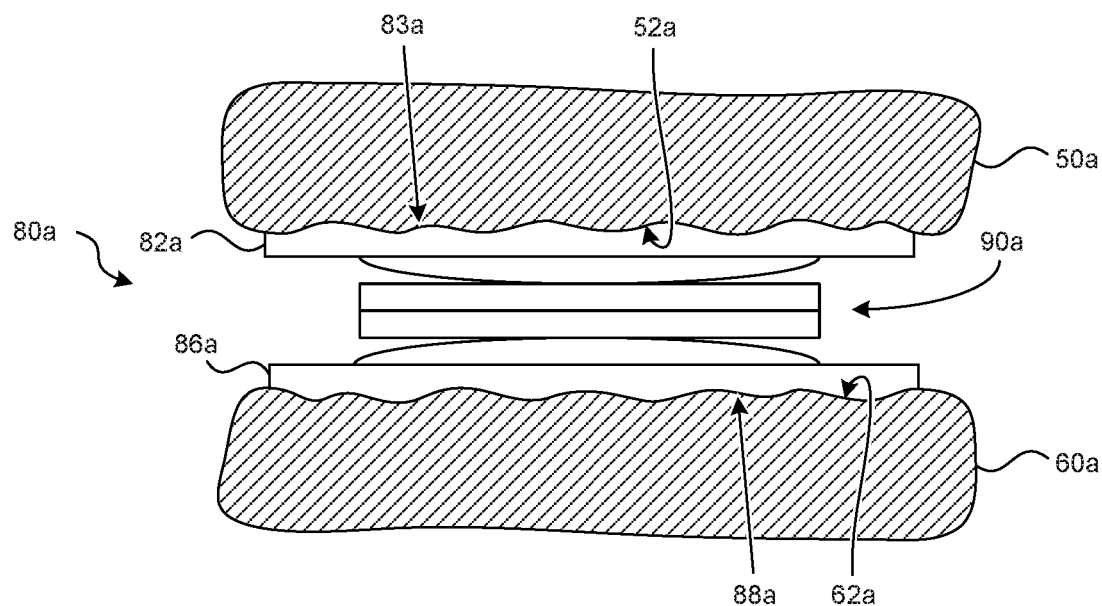
FIG. 1C is a schematic illustration of another patient-specific spinal implant positioned between vertebral bodies and in a first configuration in accordance with select embodiments of the present technology.
Figure 1D:
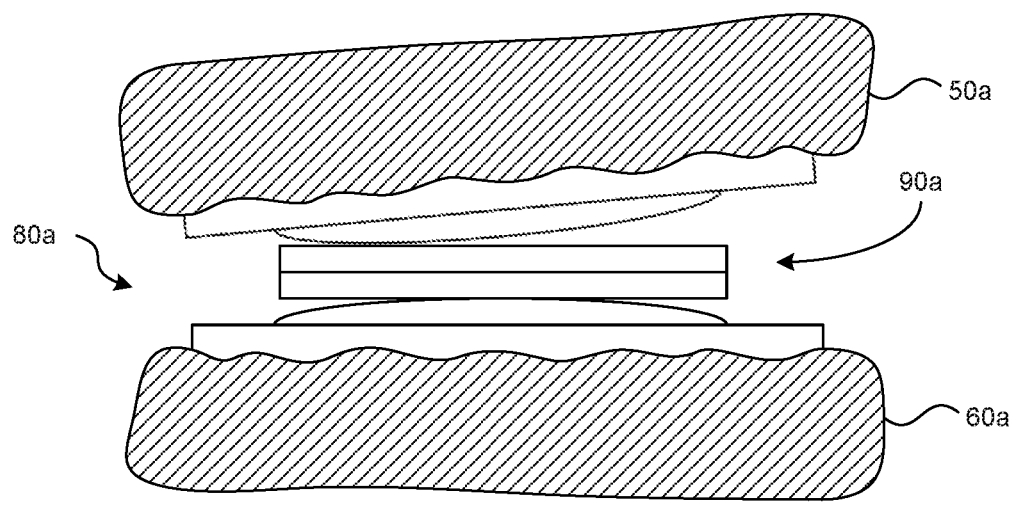
FIG. 1D is a schematic illustration of the spinal implant of FIG. 1C in a second configuration.

FIGS. 1C and 1D illustrate another patient-specific artificial disc implant 80a (referred to as "implant 80a") configured in accordance with embodiments of the present technology. As with implant 80, the implant 80a can be configured for placement between a first vertebral body 50a and a second vertebral body 60a. The implant 80a can include a first endplate 82a and a second endplate 86a. The first endplate 82a can include an outer surface 83a designed to mate with a surface 52a of a first vertebral body 50a. The second endplate 86a can include an outer surface 87a designed to mate with a surface 62a of a second vertebral body 60a. The core 90a can permit the first endplate 82a and/or the second endplate 86a to pivot or otherwise rotate relative to one another to accommodate motion between the first vertebral body 50a and the second vertebral body 60a.

As one skilled in the art will appreciate from the disclosure herein, the implants 80, 80a are provided as simple schematic examples of patient-specific artificial discs. Because the patient-specific implants described herein are designed to match individual patient anatomy, the size, shape, and geometry of the patient-specific implant will vary according to individual patient anatomy. The present technology is thus not limited to any particular artificial disc design or configuration, and can therefore include other artificial disc implants beyond those illustrated or described herein, including replacements for other discs or joints not expressly described herein.

Systems for Designing and Manufacturing Artificial Disc Implant

Figure 2:
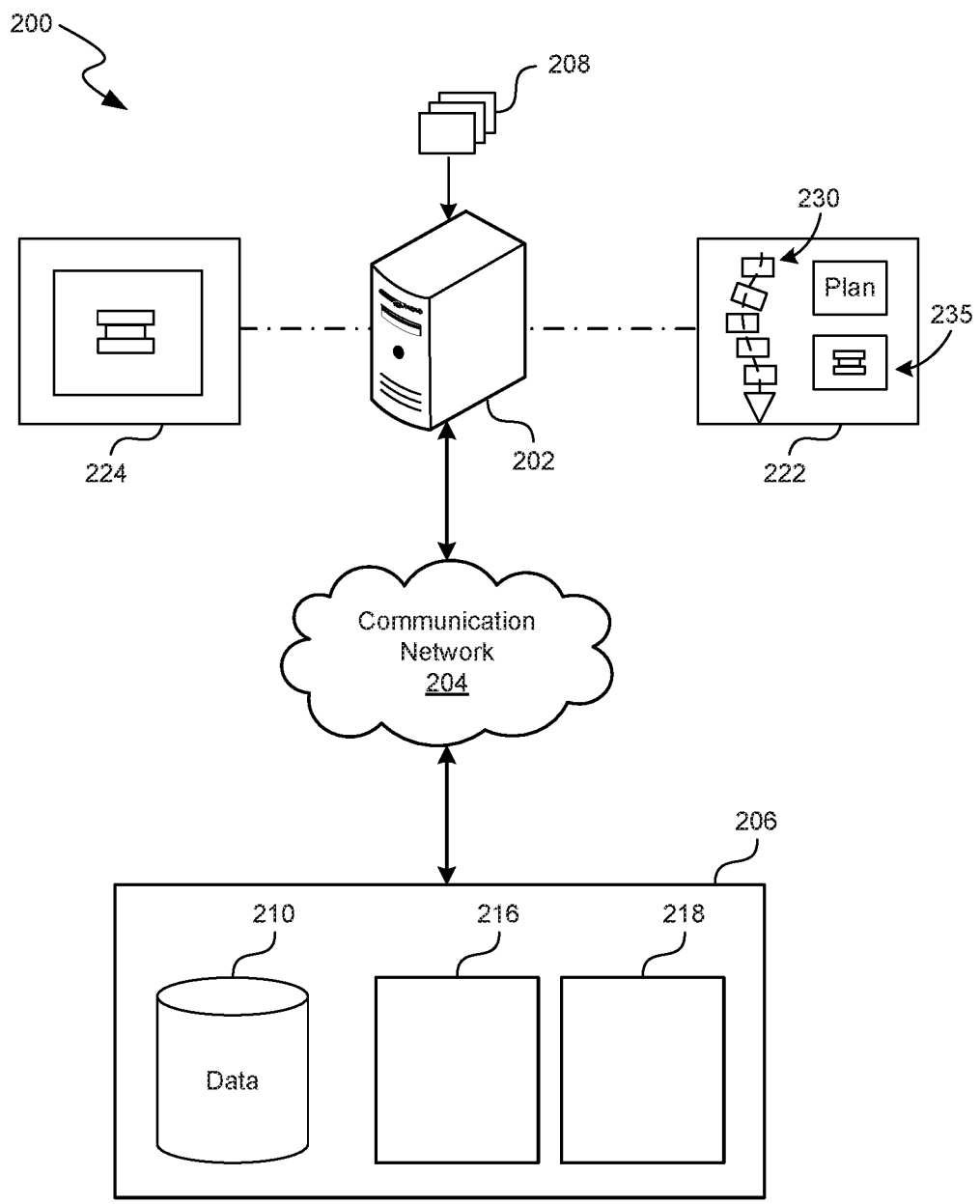
FIG. 2 is a network connection diagram illustrating a system for providing patient-specific medical care and configured in accordance with select embodiments of the present technology.

FIG. 2 is a network connection diagram illustrating a computing system 200 for providing patient-specific devices in accordance with embodiments of the present technology. The system 200 can include, among other things, a computing device 202, a communication network 204, a server 206, a display 222, and a manufacturing system 224. As described in greater detail below, the system 200 can be used to design patient-specific medical devices, such as patient-specific artificial discs, that fit native patient anatomy and/or a target anatomical configuration while also replicating and/or approximating the kinematics of a healthy or "normal" joint. Accordingly, in at least some embodiments, the system 200 can be used as part of a treatment plan for addressing degenerative disc disease or another disorder resulting in the need for a disc replacement.

The computing device 202 can be a user device, such as a smart phone, mobile device, laptop, desktop, personal computer, tablet, phablet, or other such devices known in the art. As discussed further herein, the computing device 202 can include one or more processors, and memory storing instructions executable by the one or more processors to perform the methods described herein. The computing device 202 can be associated with a healthcare provider that is treating the patient. Although FIG. 1 illustrates a single computing device 202, in alternative embodiments, the computing device 202 can instead be implemented as a client computing system encompassing a plurality of computing devices, such that the operations described herein with respect to the computing device 202 can instead be performed by the computing system and/or the plurality of computing devices.

The computing device 202 is configured to obtain (e.g., receive, determine, etc.) a patient data set 208 associated with a patient to be treated. The patient data set 208 can include image data and/or kinematic data of the patient's spine. Image data can include, for example, Magnetic Resonance Imaging (MRI) images, ultrasound images, Computerized Aided Tomography (CAT) scan images, Positron Emission Tomography (PET) images, X-Ray images (e.g., bi-planar radiography), camera images, and the like. The image data may show patient anatomy, such as the geometry, orientation, and topography of various anatomical features. In some embodiments, for example, the image data may show (and/or be used to determine) vertebral spacing, vertebral orientation, vertebral translation, abnormal bony growth, abnormal joint growth, joint inflammation, joint degeneration, tissue degeneration, stenosis, scar tissue, lumbar lordosis, Cobb angle(s), pelvic incidence, disc height, segment flexibility, rotational displacement, and other spinal tissue characteristics. Kinematic data can include, for example, specific values or other data corresponding to one or more kinematic parameters, such as values or other data corresponding to range of motion in three dimensions (including, e.g., flexion, extension, bending, etc.), flexion/extension arcs, left/right bending arcs, lateral bending, angle of bend, angle of rotation, displacement, and the like. The kinematic data can be obtained under a variety of conditions (e.g., load bearing, etc.). The values for the kinematic parameters can be determined based on images of the patient in different positions, measuring body position/motion, or the like. For example, characteristics of bony kinematic relationships can be determined by imaging the patient (e.g., X-ray, MRI, CAT scan, etc.) during movement, and analyzing the morphology of the patient based on the images. In some embodiments, the range of motion can be defined as a spherical range of motion, in which one vertebra moves relative to another vertebra in a spherical manner. In other embodiments, the range of motion can be defined as a relatively more complex range of motion defined by a three-dimensional curve through space. In some embodiments, and as described in greater detail below, the system 200 is configured to determine kinematic data based on the image data. In such embodiments, the patient data set 208 received by the computing device 202 does not necessarily include kinematic data.

In addition to image data and/or kinematic data, the patient data set 208 can include additional data including, but not limited to, medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, diagnostic equipment information (e.g., manufacturer, model number, specifications, user-selected settings/configurations, etc.), or any combination of the foregoing. In some embodiments, the patient data set 208 includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine.

The computing device 202 can include or be operably coupled to a display 222 for providing output to a user (e.g., clinician, surgeon, healthcare provider, patient). In some embodiments, the display 222 can include a graphical user interface (GUI) for visually depicting a virtual model 230 of one or more regions of the patient's anatomy based on the patient data set 208. The virtual model 230 can be a 2D model, a 3D model, CAD models, or other suitable models that provide a virtual representation of the patient's anatomy. The one or more regions can include, but are not limited to, regions of the patient's spine (e.g., cervical, thoracic, lumbar, and/or sacral). For example, in one embodiment, the target region may be a segment of the patient's spine between C6 and C3. In such embodiments, the virtual model 230 may include individual vertebrae between C6 and C3 and other associated anatomical structures, such as discs between the vertebrae. In other embodiments, the virtual model may include a model of the patient's entire spine (or generally the entire spine), rather than just specific segments. In some embodiments, generating the virtual model 230 from the image data includes reconstructing the two-dimensional image data containing pixels into three-dimensional volumetric data containing voxels that are representative of patient anatomy. In some embodiments, the image data and/or virtual model can be segmented to provide better viewing of individual anatomical features. The segmentable anatomical features can be any anatomy of interest, such as bones, discs, organs, etc. In some embodiments, for example, the bony anatomy (e.g., vertebrae) are segmented from other anatomy to enable independent viewing of individual bony structures (e.g., vertebrae). In some embodiments, the display 222 can include a touch screen or other input module that permits a user to optionally manipulate the virtual model 230.

The computing device 202 can also be operably connected via a communication network 204 to a server 206, thus allowing for data transfer between the computing device 202 and the server 206. The communication network 204 may be a wired and/or a wireless network. The communication network 204, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and/or other communication techniques known in the art.

The server 206, which may also be referred to as a "treatment assistance network" or "prescriptive analytics network," can include one or more computing devices and/or systems. As discussed further herein, the server 206 can include one or more processors, and memory storing instructions executable by the one or more processors to perform the methods described herein. In some embodiments, the server 206 is implemented as a distributed "cloud" computing system or facility across any suitable combination of hardware and/or virtual computing resources.

The computing device 202 and server 206 can individually or collectively perform the various methods described herein for providing patient-specific medical care. For example, some or all of the steps of the methods described herein can be performed by the computing device 202 alone, the server 206 alone, or a combination of the computing device 202 and the server 206. Thus, although certain operations are described herein with respect to the server 206, it shall be appreciated that these operations can also be performed by the computing device 202, and vice-versa.

The server 206 includes at least one database 210 configured to store reference data useful for the treatment planning methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from imaging studies, data from simulations, clinical trials, demographic data, treatment data, outcome data, mortality rates, or the like.

In some embodiments, the database 210 includes a plurality of reference patient data sets, each patient reference data set associated with a corresponding reference patient. For example, the reference patient can be a patient that previously received treatment or is currently receiving treatment. Each reference patient data set can include data representative of the corresponding reference patient's condition, anatomy, pathology, kinematics, medical history, preferences, and/or any other information or parameters relevant to the reference patient, such as any of the data described herein with respect to the patient data set 208. In some embodiments, the reference patient data set includes pre-operative data, intra-operative data, and/or post-operative data. For example, a reference patient data set can include data representing one or more of anatomy data, kinematic data, motion data, patient ID, age, gender, BMI, lumbar lordosis, Cobb angle(s), pelvic incidence, disc height, segment flexibility, bone quality, rotational displacement, and/or treatment level of the spine.

In some embodiments, the server 206 receives at least some of the reference patient data sets from a plurality of healthcare provider computing systems. Each healthcare provider computing system can include at least one reference patient data set (e.g., reference patient data sets) associated with reference patients treated by the corresponding healthcare provider. The reference patient data sets can include, for example, kinematic records, electronic medical records, electronic health records, biomedical data sets, etc.

As described in further detail herein, the server 206 can be configured with one or more algorithms that generate patient-specific treatment plan data (e.g., patient-specific treatment procedures, patient-specific implants) based on the reference data. In some embodiments, the patient-specific data is generated based on correlations between the patient data set 208 and the reference data. Optionally, the server 206 can predict outcomes, including recovery times, efficacy based on clinical end points, likelihood of success, predicted mortality, predicted related follow-up surgeries, or the like. In some embodiments, the server 206 can continuously or periodically analyze patient data (including patient data obtained during the patient stay) to determine near real-time or real-time risk scores, mortality prediction, etc.

In some embodiments, the server 206 includes one or more modules for performing one or more steps of the patient-specific treatment planning methods described herein. For example, in the depicted embodiment, the server 206 includes a data analysis module 216 and a treatment planning or implant design module 218. In alternative embodiments, one or more of these modules may be combined with each other, or may be omitted. Thus, although certain operations are described herein with respect to a particular module or modules, this is not intended to be limiting, and such operations can be performed by a different module or modules in alternative embodiments.

The data analysis module 216 is configured with one or more algorithms for identifying a subset of reference data from the database 210 that is likely to be useful in developing a patient-specific treatment plan. For example, the data analysis module 216 can compare patient-specific data (e.g., the patient data set 208 received from the computing device 202) to the reference data from the database 210 (e.g., the reference patient data sets) to identify similar data (e.g., one or more similar patient data sets in the reference patient data sets). The comparison can be based on one or more parameters, such as age, gender, BMI, pathology, kinematics, lumbar lordosis, pelvic incidence, and/or treatment levels. The parameter(s) can be used to calculate a similarity score for each reference patient. The similarity score can represent a statistical correlation between the patient data set 208 and the reference patient data set. Accordingly, similar patients can be identified based on whether the similarity score is above, below, or at a specified threshold value. For example, as described in greater detail below, the comparison can be performed by assigning values to each parameter and determining the aggregate difference between the subject patient and each reference patient. Reference patients whose aggregate difference is below a threshold can be considered to be similar patients.

The data analysis module 216 can further be configured with one or more algorithms to select a subset of the reference patient data sets, e.g., based on similarity to the patient data set 208 and/or treatment outcome of the corresponding reference patient. For example, the data analysis module 216 can identify one or more similar patient data sets in the reference patient data sets, and then select a subset of the similar patient data sets based on whether the similar patient data set includes data indicative of a favorable or desired treatment outcome. The outcome data can include data representing one or more outcome parameters, such as corrected anatomical metrics, range of motion, kinematic data, HRQL, activity level, complications, recovery times, efficacy, mortality, or follow-up surgeries. As described in further detail below, in some embodiments, the data analysis module 216 calculates an outcome score by assigning values to each outcome parameter. A patient can be considered to have a favorable outcome if the outcome score is above, below, or at a specified threshold value.

In some embodiments, the data analysis module 216 selects a subset of the reference patient data sets based at least in part on user input (e.g., from a clinician, surgeon, physician, healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the healthcare provider or physician can select the set of similarity and/or outcome parameters (or define new similarity and/or outcome parameters) used to generate the similarity and/or outcome score, respectively.

In some embodiments, the data analysis module 216 includes one or more algorithms used to select a set or subset of the reference patient data sets based on criteria other than patient parameters. For example, the one or more algorithms can be used to select the subset based on healthcare provider parameters (e.g., based on healthcare provider ranking/scores such as hospital/physician expertise, number of procedures performed, hospital ranking, etc.) and/or healthcare resource parameters (e.g., diagnostic equipment, facilities, surgical equipment such as surgical robots), or other non-patient related information that can be used to predict outcomes and risk profiles for procedures for the present healthcare provider. For example, reference patient data sets with images captured from similar diagnostic equipment can be aggregated to reduce or limit irregularities due to variation between diagnostic equipment. Additionally, patient-specific treatment plans can be developed for a particular health-care provider using data from similar healthcare providers (e.g., healthcare providers with traditionally similar outcomes, physician expertise, surgical teams, etc.). In some embodiments, reference healthcare provider data sets, hospital data sets, physician data sets, surgical team data sets, post-treatment data set, and other data sets can be utilized. By way of example, a patient-specific treatment plan to perform a battlefield surgery can be based on reference patient data from similar battlefield surgeries and/or datasets associated with battlefield surgeries. In another example, the patient-specific treatment plan can be generated based on available robotic surgical systems. The reference patient data sets can be selected based on patients that have been operated on using comparable robotic surgical systems under similar conditions (e.g., size and capabilities of surgical teams, hospital resources, etc.).

The implant design module 218 is configured with one or more algorithms to generate at least one treatment plan (e.g., pre-operative plans, surgical plans, post-operative plans etc.) and/or implant design based on, for example, the output from the data analysis module 216. In some embodiments, the implant design module 218 is configured to develop and/or implement at least one predictive model for generating the patient-specific treatment plan, also known as a "prescriptive model." The predictive model(s) can be developed using clinical knowledge, statistics, machine learning, AI, neural networks, or the like. In some embodiments, the output from the data analysis module 216 is analyzed (e.g., using statistics, machine learning, neural networks, AI, etc.) to identify correlations between data sets, patient parameters, healthcare provider parameters, healthcare resource parameters, treatment procedures, medical device designs, and/or treatment outcomes. These correlations can be used to develop at least one predictive model that predicts the likelihood that a treatment plan will produce a favorable outcome for the particular patient. The predictive model(s) can be validated, e.g., by inputting data into the model(s) and comparing the output of the model to the expected output.

In some embodiments, the implant design module 218 is configured to generate the implant design based on previous treatment data from reference patients. For example, the implant design module 218 can receive a selected subset of reference patient data sets and/or similar patient data sets from the data analysis module 216, and determine or identify treatment data from the selected subset. The treatment data can include, for example, range of motion and/or other kinematic data, treatment procedure data (e.g., surgical procedure or intervention data) and/or medical device design data (e.g. implant design data) that are associated with favorable or desired treatment outcomes for the corresponding patient. The implant design module 218 can analyze the treatment procedure data and/or medical device design data to determine an optimal treatment protocol for the patient to be treated. For example, the treatment procedures and/or medical device designs can be assigned values and aggregated to produce a treatment score. The patient-specific treatment plan can be determined by selecting treatment plan(s) based on the score (e.g., higher or highest score; lower or lowest score; score that is above, below, or at a specified threshold value). The personalized patient-specific treatment plan can be based on, at least in part, the patient-specific technologies or patient-specific selected technology.

Alternatively or in combination, the implant design module 218 can generate the implant designs based on correlations between data sets. For example, the implant design module 218 can correlate implant designs and medical device design data from implant designs for similar patients with favorable outcomes (e.g., as identified by the data analysis module 216). Correlation analysis can include transforming correlation coefficient values to values or scores. The values/scores can be aggregated, filtered, or otherwise analyzed to determine one or more statistical significances. These correlations can be used to determine treatment procedure(s) and/or medical device design(s) that are optimal or likely to produce a favorable outcome for the patient to be treated.

Alternatively or in combination, the implant design module 218 can generate designs using one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the implant design module 218 generates the treatment plan using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in database 210, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training dataset can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate a treatment plan, the patient data set 208 can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient. Based on these calculations, the trained machine learning model(s) can select at least one treatment plan for the patient. In embodiments where multiple trained machine learning models are used, the models can be run sequentially or concurrently to compare outcomes and can be periodically updated using training data sets. The implant design module 218 can use one or more of the machine learning models based the model's predicted accuracy score.

The patient-specific treatment plan generated by the implant design module 218 can include at least one patient-specific treatment procedure (e.g., a surgical procedure or intervention) and/or at least one patient-specific medical device (e.g., an implant or implant delivery instrument). A patient-specific treatment plan can include an entire surgical procedure or portions thereof. Additionally, one or more patient-specific medical devices can be specifically selected or designed for the corresponding surgical procedure, thus allowing for the various components of the patient-specific technology to be used in combination to treat the patient. In some embodiments, the patient-specific medical device design includes a design for an orthopedic implant and/or a design for an instrument for delivering an orthopedic implant. Examples of such implants include, but are not limited to, screws (e.g., bone screws, spinal screws, pedicle screws, facet screws), interbody implant devices (e.g., intervertebral implants), cages, plates, rods, discs, fusion devices, spacers, rods, expandable devices, stents, brackets, ties, scaffolds, fixation device, anchors, nuts, bolts, rivets, connectors, tethers, fasteners, joint replacements, hip implants, or the like. Examples of instruments include, but are not limited to, screw guides, cannulas, ports, catheters, insertion tools, or the like.

A patient-specific medical device design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of a corresponding medical device. For example, a design for an orthopedic implant can include implant shape, size, material, and/or effective stiffness (e.g., lattice density, number of struts, location of struts, etc.). In some embodiments, the generated patient-specific medical device design is a design for an entire device. Alternatively, the generated design can be for one or more components of a device, rather than the entire device.

In some embodiments, the design is for one or more patient-specific device components that can be used with standard, off-the-shelf components. For example, in a spinal surgery, a pedicle screw kit can include both standard components and patient-specific customized components. In some embodiments, the generated design is for a patient-specific medical device that can be used with a standard, off-the-shelf delivery instrument. For example, the implants (e.g., screws, screw holders, rods) can be designed and manufactured for the patient, while the instruments for delivering the implants can be standard instruments. This approach allows the components that are implanted to be designed and manufactured based on the patient's anatomy and/or surgeon's preferences to enhance treatment. The patient-specific devices described herein are expected to improve delivery into the patient's body, placement at the treatment site, and/or interaction with the patient's anatomy.

In embodiments in which the patient-specific treatment plan includes a surgical procedure to implant a medical device, the implant design module 218 can also store various types of implant surgery information, such as implant parameters (e.g., types, dimensions), availability of implants, aspects of a pre-operative plan (e.g., initial implant configuration, detection and measurement of the patient's anatomy, etc.), FDA requirements for implants (e.g., specific implant parameters and/or characteristics for compliance with FDA regulations), or the like. In some embodiments, the implant design module 218 can convert the implant surgery information into formats useable for machine-learning based models and algorithms. For example, the implant surgery information can be tagged with particular identifiers for formulas or can be converted into numerical representations suitable for supplying to the trained machine learning model(s). The implant design module 218 can also store information regarding the patient's anatomy, such as two- or three-dimensional images or models of the anatomy, and/or information regarding the biology, geometry, and/or mechanical properties of the anatomy. The anatomy information can be used to inform implant design and/or placement.

The treatment plan(s) generated by the implant design module 218 can be transmitted via the communication network 204 to the computing device 202 for output to a user (e.g., clinician, surgeon, healthcare provider, patient) via the display 222. As described previously, the display 222 can include a graphical user interface (GUI) for visually depicting various aspects of the treatment plan(s). For example, the display 222 can show various aspects of a surgical procedure to be performed on the patient, such as the surgical approach, treatment levels, corrective maneuvers, tissue resection, and/or implant placement. In addition to the virtual model 230 previously described, the display 222 can also show a design or rendering 235 of the patient-specific implant, such as a two- or three-dimensional model of the implant. The display 222 can also show patient information, such as two- or three-dimensional images or models of the patient's anatomy where the surgical procedure is to be performed and/or where the device is to be implanted. The computing device 202 can further include one or more user input devices (not shown) allowing the user to modify, select, approve, and/or reject the displayed treatment plan(s).

In some embodiments, the medical device design(s) generated by the implant design module 218 can be transmitted from the computing device 202 and/or server 206 to a manufacturing system 224 for manufacturing a corresponding medical device. The manufacturing system 224 can be located on site or off site. On-site manufacturing can reduce the number of sessions with a patient and/or the time to be able to perform the surgery whereas off-site manufacturing can be useful make the complex devices. Off-site manufacturing facilities can have specialized manufacturing equipment. In some embodiments, more complicated device components can be manufactured off site, while simpler device components can be manufactured on site.

Various types of manufacturing systems are suitable for use in accordance with the embodiments herein. For example, the manufacturing system 224 can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively or in combination, the manufacturing system 224 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 224 can manufacture one or more patient-specific medical devices based on fabrication instructions or data (e.g., CAD data, 3D data, digital blueprints, stereolithography data, or other data suitable for the various manufacturing technologies described herein). In some embodiments, the patient-specific medical device can include features, materials, and designs shared across designs to simplify manufacturing. For example, implants for different patients can have similar internal deployment mechanisms but have different deployed configurations. In some embodiments, the components of the patient-specific medical devices are selected from a set of available pre-fabricated components and the selected pre-fabricated components can be modified based on the fabrication instructions or data.

The treatment plans described herein can be performed by a surgeon, a surgical robot, or a combination thereof, thus allowing for treatment flexibility. In some embodiments, the surgical procedure can be performed entirely by a surgeon, entirely by a surgical robot, or a combination thereof. For example, one step of a surgical procedure can be manually performed by a surgeon and another step of the procedure can be performed by a surgical robot. In some embodiments the implant design module 218 generates control instructions configured to cause a surgical robot (e.g., robotic surgery systems, navigation systems, etc.) to partially or fully perform a surgical procedure. The control instructions can be transmitted to the robotic apparatus by the computing device 202 and/or the server 206.

Following the treatment of the patient in accordance with the treatment plan, treatment progress can be monitored over one or more time periods to update the data analysis module 216 and/or implant design module 218. Post-treatment data can be added to the reference data stored in the database 210. The post-treatment data can be used to train machine learning models for developing patient-specific treatment plans, patient-specific medical devices, or combinations thereof.

It shall be appreciated that the components of the system 200 can be configured in many different ways. For example, in alternative embodiments, the database 210, the data analysis module 216 and/or the implant design module 218 can be components of the computing device 202, rather than the server 206. As another example, the database 210 the data analysis module 216, and/or the implant design module 218 can be located across a plurality of different servers, computing systems, or other types of cloud-computing resources, rather than at a single server 206 or computing device 202.

Additionally, in some embodiments, the system 200 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like. In some embodiments, the system 200 may include additional features and/or capabilities, such as any of those described in U.S. application Ser. No. 16/735,222, filed Jan. 6, 2020, the disclosure of which is incorporated by reference herein in its entirety.

Figure 3:
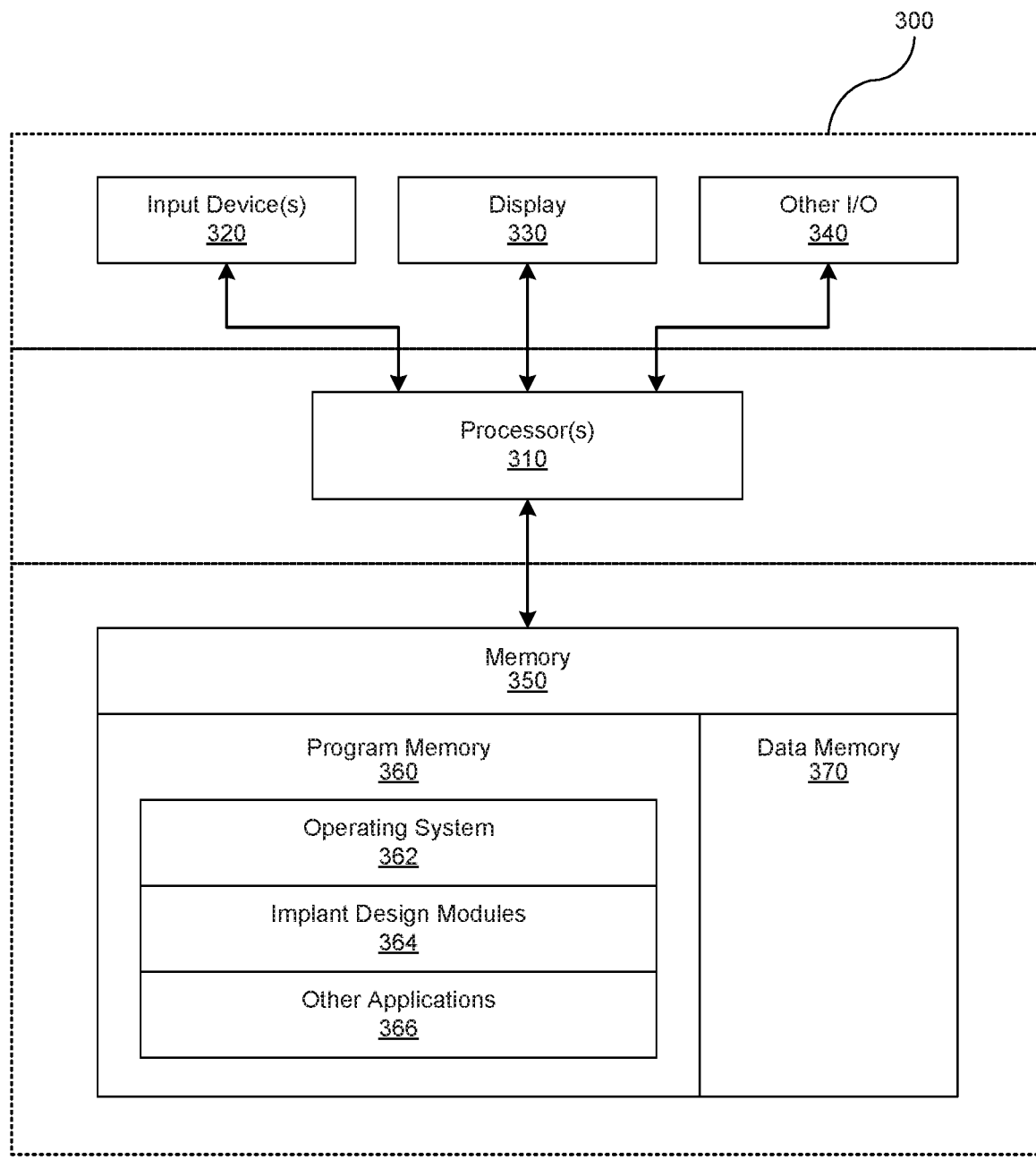
FIG. 3 illustrates a computing device suitable for use in connection with the system of FIG. 1, in accordance with select embodiments of the present technology.

FIG. 3 illustrates a computing device 300 suitable for use in connection with the system 200 of FIG. 2, according to an embodiment. The computing device 300 can be incorporated in various components of the system 200 of FIG. 2, such as the computing device 202 or the server 206. The computing device 300 includes one or more processors 310 (e.g., CPU(s), GPU(s), HPU(s), etc.). The processor(s) 310 can be a single processing unit or multiple processing units in a device or distributed across multiple devices. The processor(s) 310 can be coupled to other hardware devices, for example, with the use of a bus, such as a PCI bus or SCSI bus. The processor(s) 310 can be configured to execute one or more computer-readable program instructions, such as program instructions to carry out of any of the methods described herein.

The computing device 300 can include one or more input devices 320 that provide input to the processor(s) 310, e.g., to notify it of actions from a user of one or more aspects of the computing device 300. The actions can be mediated by a hardware controller that interprets the signals received from the input device 320 and communicates the information to the processor(s) 310 using a communication protocol. Input device(s) 320 can include, for example, a mouse, a keyboard, a touchscreen, an infrared sensor, a touchpad, a wearable input device, a camera- or image-based input device, a microphone, or other user input devices.

The computing device 300 can include a display 330 used to display various types of output, such as text, models, virtual procedures, surgical plans, implants, graphics, and/or images (e.g., images with voxels indicating radiodensity units or Hounsfield units representing the density of the tissue at a location). For example, in some embodiments the display 330 provides a two or three-dimensional virtual model of a patient's spine. In some embodiments, the display 330 provides graphical and textual visual feedback to a user. The processor(s) 310 can communicate with the display 330 via a hardware controller for devices. In some embodiments, the display 330 includes the input device(s) 320 as part of the display 330, such as when the input device(s) 320 include a touchscreen or is equipped with an eye direction monitoring system. In alternative embodiments, the display 330 is separate from the input device(s) 320. Examples of display devices include an LCD display screen, an LED display screen, a projected, holographic, or augmented reality display (e.g., a heads-up display device or a head-mounted device), and so on. In some embodiments, the display 330 is configured to display a virtual model of a patient's spine generated based on received patient data (e.g., image data), as previously described with respect to display 222.

Optionally, other I/O devices 340 can also be coupled to the processor(s) 310, such as a network card, video card, audio card, USB, firewire or other external device, camera, printer, speakers, CD-ROM drive, DVD drive, disc drive, or Blu-Ray device. Other I/O devices 340 can also include input ports for information from directly connected medical equipment such as imaging apparatuses, including MRI machines, X-Ray machines, CT machines, etc. Other I/O devices 340 can further include input ports for receiving data from these types of machine from other sources, such as across a network or from previously captured data, for example, stored in a database.

In some embodiments, the computing device 300 also includes a communication device (not shown) capable of communicating wirelessly or wire-based with a network node. The communication device can communicate with another device or a server through a network using, for example, TCP/IP protocols. The computing device 300 can utilize the communication device to distribute operations across multiple network devices, including imaging equipment, manufacturing equipment, etc.

The computing device 300 can include memory 350, which can be in a single device or distributed across multiple devices. Memory 350 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy discs, CDs, DVDs, magnetic storage devices, tape drives, device buffers, and so forth. A memory is not a propagating signal divorced from underlying hardware; a memory is thus non-transitory. In some embodiments, the memory 350 is a non-transitory computer-readable storage medium that stores, for example, programs, software, data, or the like. In some embodiments, memory 350 can include program memory 360 that stores programs and software, such as an operating system 362, one or more implant design modules 364, and other application programs 366. The implant design module(s) 364 can include one or more modules configured to perform the various methods described herein. Memory 350 can also include data memory 370 that can include, e.g., reference data, configuration data, settings, user options or preferences, etc., which can be provided to the program memory 360 or any other element of the computing device 300.

Methods for Designing Patient-Specific Devices

Figure 4:
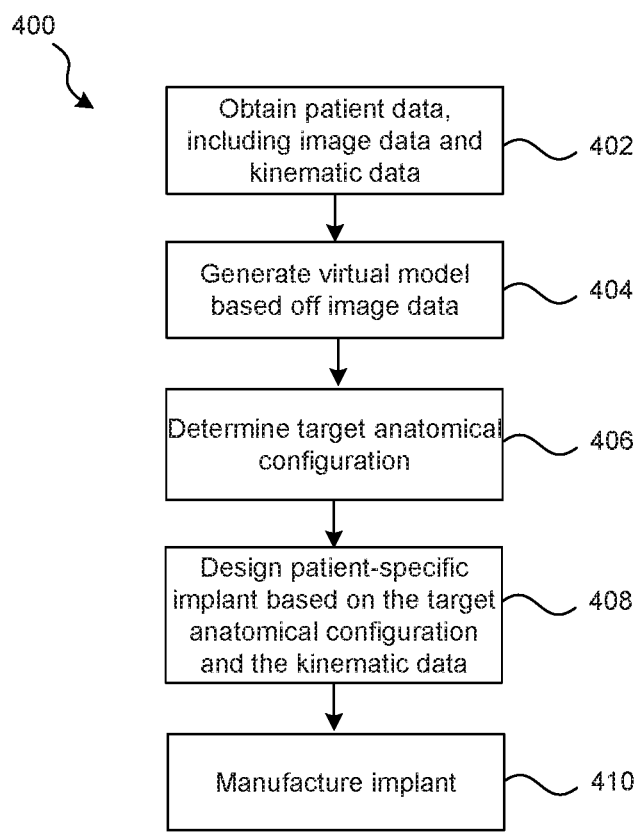
FIG. 4 is a flow diagram illustrating a method for designing a patient-specific implant in accordance with select embodiments of the present technology.

FIG. 4 is a flowchart of a method 400 for designing a patient-specific implant in accordance with select embodiments of the present technology. For example, the method 400 can be used to design a patient-specific artificial disc implant. The method 400 can begin in step 402 by obtaining patient data. Patient data can include image data and kinematic data of the patient's spine. Image data can include, for example, Magnetic Resonance Imaging (MRI) images, ultrasound images, Computerized Aided Tomography (CAT) scan images, Positron Emission Tomography (PET) images, X-Ray images (e.g., bi-planar radiography), camera images, and the like. The image data may show patient's native anatomical configuration (e.g., pre-operative anatomy), such as the geometry, orientation, and topography of various anatomical features. In some embodiments, for example, the image data may show (and/or be used to determine) vertebral spacing, vertebral orientation, vertebral translation, abnormal bony growth, abnormal joint growth, joint inflammation, joint degeneration, tissue degeneration, stenosis, scar tissue, lumbar lordosis, Cobb angle(s), pelvic incidence, disc height, segment flexibility, rotational displacement, and other spinal tissue characteristics.

Kinematic data can include, for example, specific values or other data corresponding to one or more kinematic parameters, such as values or other data corresponding to range of motion in three dimensions (including, e.g., flexion, extension, bending, etc.), flexion/extension arcs, left/right bending arcs, lateral bending, angle of bend, angle of rotation, displacement, axial rotation, and the like. The kinematic data can be obtained under a variety of conditions (e.g., load bearing, non-load bearing, etc.). In some embodiments, the range of motion can be defined as a spherical range of motion, in which one vertebra moves relative to another vertebra in a spherical manner. In other embodiments, the range of motion can be defined as a relatively more complex range of motion defined by a three-dimensional curve through space. Other patient data in addition to image data and kinematic data can optionally be obtained in step 402. Additional patient data can include, but is not limited to, medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, and/or any combination of the foregoing.

In some embodiments, obtaining the kinematic data in step 402 includes determining the values of the one or more kinematic parameters using one or more software modules (e.g., the implant design module 218 in FIG. 2 and/or the implant design module 364 in FIG. 3). The software module may perform a kinematic evaluation of the patient based on the image data and/or other patient data to estimate various kinematic parameters for the patient. For example, the software module can analyze one or more anatomical features/measurements in the image data and/or virtual model to define kinematic parameters, determine kinematic relationships, and/or estimate various kinematic parameters. Suitable anatomical features/measurements include, but are not limited to, distance between anatomical landmarks, fiducials, vertebral spacing, vertebral orientation, abnormal bony growth, abnormal joint growth, joint inflammation, joint degeneration, tissue degeneration, stenosis, scar tissue, and combinations thereof. Other patient data that can be used by the software module to estimate the kinematic parameters includes, but is not limited to, medical history, sex, age, height, weight, and the like. In some embodiments, the software module may incorporate one or more artificial intelligence architectures for determining the various kinematic parameters based on the image data.

The artificial intelligence architectures can be similar to those previously described herein, and can include, for example, trained neural networks (e.g., trained convolutional neural networks, etc.) for analyzing two-dimensional images and/or three-dimensional models. Without being bound by theory, using the one or more software modules to perform the kinematic evaluation can reduce and/or eliminate the need to conduct a manual evaluation of the patient's kinematics before the implant surgery. However, in at least some embodiments, the kinematic data can be obtained through one or more standard kinematic studies. Therefore, in at least some embodiments, obtaining the kinematic data in step 402 includes receiving the values of the one or more kinematic parameters. For example, the values of the one or more kinematic parameters can be obtained from a motion study and inputted into a system performing the method 400 (e.g., inputted into the computing device 300 via the input device(s) 320, shown in FIG. 3) or through joint morphology studies.

The method 400 further includes generating, based at least in part on the image data obtained in step 402, a virtual model of one or more regions of the patient's anatomy in step 404. The virtual model can be a 2D model, a 3D model, CAD models, or other suitable models that provide a virtual representation of the patient's native anatomy. The one or more regions can include, but are not limited to, regions of the patient's spine (e.g., cervical, thoracic, lumbar, and/or sacral). For example, in one embodiment, the target region may be a segment of the patient's spine between C6 and C3. In such embodiments, the virtual representation may include individual vertebrae between C6 and C3 and other associated anatomical structures, such as discs between the vertebrae. In some embodiments, the virtual model may include a model of the patient's entire spine, rather than just specific segments. In some embodiments, generating the virtual model from the image data includes reconstructing the two-dimensional image data containing pixels into three-dimensional volumetric data containing voxels that are representative of patient anatomy. In some embodiments, the image data and/or virtual model can be segmented to provide better viewing of individual anatomical features. The segmentable anatomical features can be any anatomy of interest, such as bones, discs, organs, etc. In some embodiments, for example, the bony anatomy (e.g., vertebrae) are segmented from other anatomy to enable independent viewing of individual bony structures (e.g., vertebrae). The virtual model can optionally be displayed to a physician, such as via the display 222, shown in FIG. 2. In some embodiments, step 404 is omitted and the method 400 proceeds directly from step 402 to step 406.

In step 406, a user (e.g., a surgeon or other physician) and/or a software module (e.g., the implant design module 218 and/or the implant design module 364) determines a target anatomical configuration for the one or more regions of the patient's anatomy. The target anatomical configuration can be different than the native anatomical configuration shown in the image data. The target anatomical configuration can include an adjustment to one or more anatomical features relative to the native anatomical configuration, including, but not limited to, an adjustment to spacing between vertebral bodies, orientation of vertebral bodies, alignment of two or more vertebral bodies, lumbar lordosis, Cobb angle(s), pelvic incidence, disc height, segment flexibility, rotational displacement, and the like. For example, in embodiments in which the patient has vertebral disc degeneration between two vertebrae, the image data may illustrate that the native anatomical configuration has a reduced or sub-optimal distance between an inferior boundary of a first vertebra and a superior boundary of the second vertebra. The target anatomical configuration may therefore include an increased distance between the first and second vertebrae that is reflective of a "healthy" or "normal" anatomy. In another example, the image data may illustrate that a first vertebra is out of alignment with a second vertebra. In such embodiments, the target anatomical configuration may therefore include realigning the first vertebra and the second vertebra.

In embodiments in which a user determines the target anatomical configuration, the user can use the virtual model to manipulate one or more relationships (distances, angles, constraints, etc.) between individual vertebrae to set the target anatomical configuration. Manipulations can include, but are not limited to, translation along an axis or curve, rotation about an axis or centroid, and/or rotation about the center of mass. In some embodiments, the manipulation can be done until the virtual model illustrates the anatomy in a "desired" anatomical configuration. The user can then provide an input setting the illustrated desired anatomical configuration as the target anatomical configuration.

In embodiments in which a software module determines the target anatomical configuration, the software module may automatically manipulate the virtual model to provide a recommend target anatomical configuration based on one or more design criteria and/or reference patient data sets. Suitable design criteria can include, for example, target values associated with various anatomical features, including, for example, target values associated with vertebral spacing (e.g., minimum vertebral body spacing, maximum vertebral spacing, etc.), vertebral orientation, vertebral alignment, vertebral translation, lumbar lordosis, Cobb angle(s), pelvic incidence, disc height, segment flexibility, rotational displacement, kinematics, or the like. Suitable reference patient data sets can be identified using, for example, the data analysis module 216 described previously with reference to FIG. 2. The implant design module can further perform one or more simulations, analyses (e.g., stress analysis, fatigue analysis, etc.), or the like to provide feedback (e.g., identified high stress regions), design recommendations, treatment recommendations (e.g., steps to prepare implantation site), or the like. The software module used in step 406 to manipulate the virtual model and provide a recommended target anatomical configuration can be the same as or different than the software module used in step 402 to conduct the kinematic evaluation. In some embodiments, determining the target anatomical configuration includes using the software module to provide a recommend target anatomical configuration, and then permitting the physician to optionally further modify the target anatomical configuration.

The method 400 continues by designing a patient-specific implant in step 408. The patient-specific implant can be designed using the software module, which can be the same as or different than the software modules optionally used in steps 402 and 408. Among other things, the software module designs the patient-specific implant to match the target anatomical configuration when it is implanted in the patient. Accordingly, the patient-specific implant should fit in the negative space (e.g., the "implant envelope") of the target anatomical configuration. The negative space can be used to determine various geometric parameters of the patient-specific implant. The geometric parameters include, but are not limited to, dimensions, heights, surfaces, footprints, and the like. In some embodiments, a virtual patient-specific implant can be created and shown within the negative space of the virtual representation of the patient anatomy.

The software module can also design the patient-specific implant to match the anatomical topography of the target region. For artificial disc implants, this includes matching the topography of the disc endplates to the topography of the adjacent vertebrae. For example, referring back to FIG. 1A, the outer surface 83 of the first endplate 82 is designed to mate with the topography of the inferior surface 52 of the relatively superior vertebra 50, while the outer surface 87 of the second endplate 86 is designed to mate with the topography of the superior surface 62 of the relatively inferior vertebra 60. For example, if the inferior surface of the relatively superior vertebra is slightly convex, the outer surface of the first endplate will be designed as slightly concave to "mate" with the slightly convex vertebral surface. Without being bound by theory, increasing the fit (e.g., forming a gapless or generally gapless interface) between the implant endplates and the vertebrae is expected to prevent and/or reduce instances of dynamic failure of the implants (e.g., by reducing and/or preventing micro-motions of the implant), and/or increase the efficacy of the implants.

In some embodiments, the software module can further design the patient-specific implant to improve the one or more kinematic parameter values obtained in step 402. For example, as described in greater detail with reference to FIG. 5, the obtained kinematic parameter values may show that the patient's kinematics are limited by the diseased joint that is being replaced by the patient-specific implant. Accordingly, rather than designing the patient-specific implant to maintain the sub-optimal kinematics associated with the diseased condition, the software module can design the patient-specific implant such that, when the patient-specific implant is implanted between the target vertebrae, it provides improved kinematics that meet one or more predetermined kinematic criteria (e.g., reference or "target" kinematic values).

More specifically, in some embodiments the kinematic parameter values obtained in step 402 are compared to one or more predetermined kinematic criteria, which can include the reference kinematic values. The reference kinematic values can include specific values for the various kinematic parameters, such as specific values associated with range of motion, angle of bend, angle of rotation, displacement, flexion, extension, flexion/extension arc, lateral bending, left/right bending arc, axial rotation, and the like. Depending on the specific parameter, the reference kinematic values can include a minimum threshold, a maximum threshold, and/or a range. For example, the reference kinematic values may include a flexion/extension arc of between 60 degrees and 80 degrees, between 70 degrees and 80 degrees, etc., and/or greater than 60 degrees, greater than 70 degrees, greater than 80 degrees, etc. Additionally or alternatively, the reference kinematic values may include a lateral bending minimum threshold of 25 degrees, 30 degrees, 35 degrees, etc. The reference kinematic values can be selected based on the kinematics of a normal or healthy patient of a similar age, weight, height, etc. In some embodiments, the reference kinematic values may also be selected based on one or more patient features, such as a patient's desired range of motion, overall spine health, activity-level, or the like. In some embodiments, the reference kinematic values can be determined using the reference patient data stored in the database 210 on server 206 (FIG. 2), and/or can be selected by the surgeon or other physician.

If one or more of the obtained kinematic parameter values do not meet the one or more of the corresponding reference kinematic values (and/or is not within a threshold degree of deviation from the corresponding reference kinematic parameter value, such as within 5%, within 10%, etc.), the software module can automatically design the patient-specific implant to improve the one or more kinematic parameter values. For example, the software module may design the patient-specific implant such that, when implanted in the patient, it increases arcs of flexion/extension, arcs of left/right bending, or other kinematic parameter values by at least 5%, 10%, 20%, 30%, or other suitable amounts (e.g., based on the difference between the obtained kinematic parameter values and the reference kinematic parameter values). In some procedures, the patient-specific artificial implant can increase the patient's flexion/extension arc from 50 degrees to 60 degrees, from 60 degrees to 70 degrees, from 60 degrees to 80 degrees, or other suitable amounts. In some procedures, the patient-specific artificial implant can increase the patient's lateral bending from 10 degrees to 20 degrees, from 20 degrees to 30 degrees, from 20 degrees to 40 degrees, or other suitable amounts.

In a particular example, if the obtained kinematic parameter values indicate that the patient's flexion/extension arc is 50 degrees, but the reference kinematic parameter value for the flexion/extension arc is a range between 60 degrees and 80 degrees, the software module can design the patient-specific implant such that, when it is implanted in the patient, the patient will have a flexion/extension arc of at least 60 degrees. However, in other embodiments, the software module designs the patient-specific implant to improve the flexion/extension arc, but not necessarily all the way to the reference kinematic parameter value (e.g., improves from 50 degrees to 55 degrees in the preceding example). In another example, if the obtained kinematic parameter values indicate that the patient's lateral bending (e.g., left bending) is 20 degrees, but the reference kinematic parameter value for lateral bending has a minimum threshold of 30 degrees, the software module can design the patient-specific implant such that, when it is implanted in the patient, the patient will have a lateral bending of at least 30 degrees.

In some embodiments, the software module designs the patient-specific implant to maintain (e.g., be generally similar to and/or the same as, such as within 10% of) the kinematic parameter values obtained in step 402. For example, the obtained kinematic parameter values may show that the patient's kinematics are not limited by the diseased joint that is being replaced by the patient-specific implant. This can be determined by, for example, comparing the obtained kinematic parameter values to one or more predetermined kinematic criteria (e.g., the reference kinematic values described above). If the obtained kinematic parameter values meet the one or more predetermined kinematic criteria (and/or is within a threshold degree of deviation from the reference kinematic parameter values, such as within 5%, within 10%, etc.), the software module may design the patient-specific implant such that, when the patient-specific implant is implanted between the target vertebrae, the target vertebrae have kinematics similar to and/or the same as the kinematics obtained in step 402. Accordingly, in some procedures, the patient-specific artificial disc can be configured to maintain motion of the spine (e.g., to maintain healthy kinematics, to reduce the risk of complications, etc.). For example, the patient-specific artificial disc can maintain flexion/extension arcs, degree left/right bending arcs, or the like measured using a standard arc of lumbar bending (e.g., measured in an upright and/or recumbent posture), digital measurement techniques, and/or via image analysis.

In a particular example, if the obtained kinematic parameter values indicate that the patient's flexion/extension arc is 65 degrees, and the reference kinematic parameter value for the flexion/extension arc is a range between 60 degrees and 80 degrees, the software module can design the patient-specific implant such that, when it is implanted in the patient, the patient will maintain the flexion/extension arc of about 62 degrees. In another example, if the obtained kinematic parameter values indicate that the patient's lateral bending (e.g., left bending) is 35 degrees, and the reference kinematic parameter value for lateral bending has a minimum threshold of 30 degrees, the software module can design the patient-specific implant such that, when it is implanted in the patient, the patient will maintain lateral bending of at about 35 degrees.

Designing the patient-specific implant to maintain or improve the kinematics includes designing the interior portion of the patient-specific implant to have specific motion characteristics. In particular, and referring back to FIGS. 1A and 1B, the motion segment or core 90 of the patient-specific implant can be designed to have the appropriate orientation, rotation, flexion, and/or translation to enable the target vertebrae to move relative to one another in accordance with the desired kinematics after the implant 80 is implanted in the patient. This can include selecting a combination of one or more suitable materials that provide the target kinematics. Suitable materials include, but are not limited to, elastomeric polymers, rigid polymers, hybrid materials with elastomeric and rigid properties, ceramics, metals, and combinations thereof. The motion segment can also be comprised of a plurality of mating surfaces that provide the determined kinematics. Accordingly, in some embodiments the desired kinematics can be obtained by selecting a geometry or other characteristic of the plurality of mating surfaces that provide the desired kinematics. The motion segment or core 90 can therefore be designed to provide any of the corrections previously discussed, such as improving arcs of flexion/extension, arcs of left/right bending, or other kinematic parameter values at least 5%, 10%, 20%, 30%, or other suitable amounts.

In some embodiments, the patient may have other conditions (e.g., nerve compression, a curved spine, lordosis, arthritis, etc.) that may limit kinematic parameter values. In some embodiments, the software module may therefore recommend secondary procedures to be performed on identified anatomical features (e.g., stenosis, enlarged facet joints, bony overgrowths, loss of cartilage, etc.) to further enhance or affect body motion. The predicted outcome of the secondary procedure(s) can be inputted into the software module to determine the modified/optimized patient-specific implant. Accordingly, the patient-specific implant can be modified/optimized for a spine in which the secondary procedure(s) are performed concurrently with or after implantation of the patient-specific implant. In some embodiments, the patient-specific artificial disc can also be designed to compensate, alleviate, or otherwise affect those other conditions. For example, the patient-specific artificial disc may be designed to provide a threshold amount of motion while reducing or limiting pain associated with nerve compression, correcting for lordosis, etc. In some embodiments, the patient-specific artificial implant can be designed to enable specific motion(s) suitable for performing selected tasks, such as walking, running, swinging golf clubs, jumping, etc. The selected tasks can be inputted into the software modules which then designs the implant to enable the patient to perform those tasks. The design criteria can be selected by the software module, designer, and/or physician.

The software module can design the patient-specific implant to be optimized in other ways as well. For example, the software module can analyze a virtual model of the patient-specific implant implanted in the patient anatomy to identify one or more load-bearing or otherwise high-stress regions of the implant. If the fatigue characteristics associated with the load-bearing or otherwise high stress regions exceed a maximum threshold, the processing module can automatically redesign the patient-specific implant to avoid, alter, accommodate, or otherwise account for the stress and such that the fatigue characteristics no longer exceed the maximum threshold. The patient-specific implant can also be optimized for the patient in other ways not expressly described herein.

As provided above, in at least some embodiments the patient-specific implant is designed in step 408 using one or more software modules, such as the implant design module 218 described above with respect to FIG. 2 and/or the implant design module 364 described above with respect to FIG. 3. The software module used in step 408 can be the same as or different than the software module optionally used in steps 402 and 406. Accordingly, in at least some embodiments, the patient-specific implant can be automatically designed in step 408 using the system 200 and/or computing device 300. In other embodiments, step 408 is only partially automated and can include one or more user steps/inputs.

After the patient-specific implant is designed, the method 400 can continue in step 410 by manufacturing the patient-specific implant. In some embodiments, the patient-specific implant design(s) can be transmitted from the software module to a manufacturing system for manufacturing the patient-specific implant. For example, the method can include generating computer-executable manufacturing instructions that, when executed by a manufacturing system, direct the manufacturing system to manufacture the patient-specific implant. The manufacturing instructions can be transmitted to the manufacturing system using any suitable means. The manufacturing system can be located on site or off site. On-site manufacturing can reduce the number of sessions with a patient and/or the time to be able to perform the surgery whereas off-site manufacturing can be useful make complex devices, and may have specialized manufacturing equipment. In some embodiments, more complicated device components can be manufactured off site, while simpler device components can be manufactured on site.

Various types of manufacturing systems are suitable for use in accordance with the embodiments herein. For example, the manufacturing system can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively or in combination, the manufacturing system can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system can manufacture one or more patient-specific medical devices based on fabrication instructions or data (e.g., CAD data, 3D data, digital blueprints, stereolithography data, or other data suitable for the various manufacturing technologies described herein). In some embodiments, the patient-specific implants can include features, materials, and designs shared across designs to simplify manufacturing. For example, deployable patient-specific implants for different patients can have similar internal deployment mechanisms but have different deployed configurations. In some embodiments, the components of the patient-specific implants are selected from a set of available pre-fabricated components and the selected pre-fabricated components can be modified based on the fabrication instructions or data.

Figure 5:
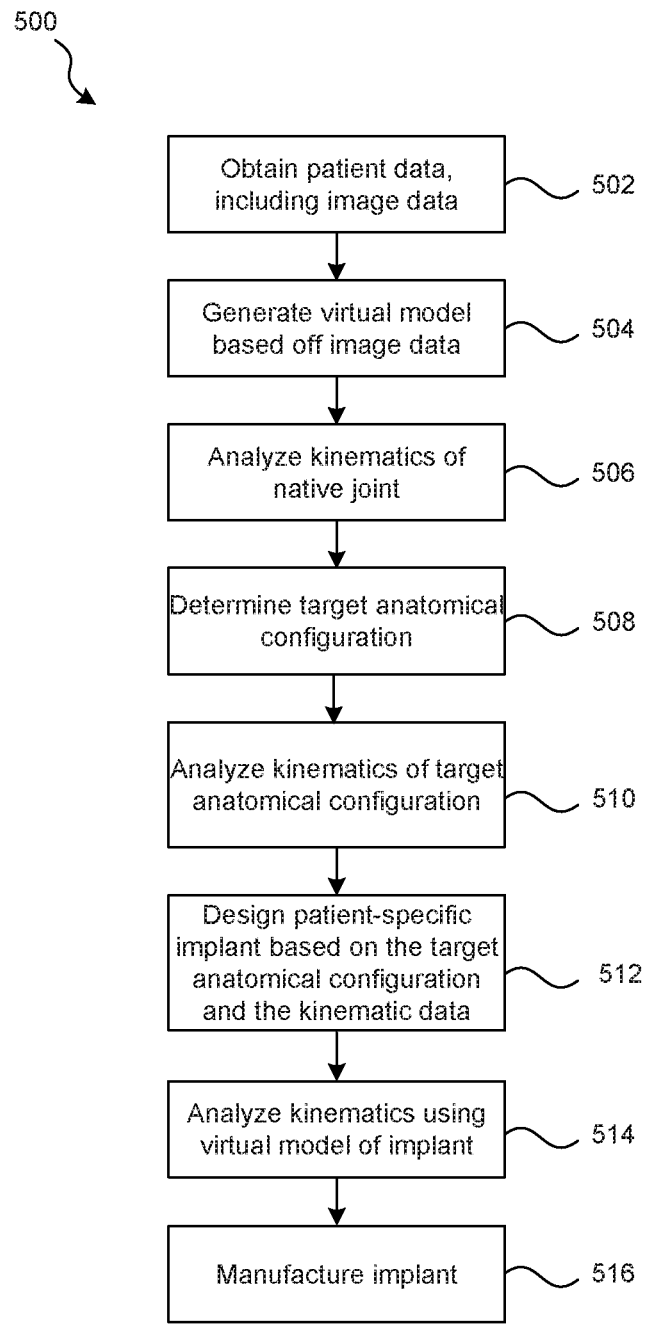
FIG. 5 is a flow diagram illustrating another method for designing a patient-specific implant in accordance with select embodiments of the present technology.

FIG. 5 is a flowchart of another method 500 for designing a patient-specific implant in accordance with select embodiments of the present technology. In particular, method 500 includes using one or more software modules (e.g., implant design module 218 and/or implant design module 364) to determine, analyze, and/or evaluate the kinematics of a native joint and to design a patient-specific implant based on the determined kinematics. Accordingly, in some embodiments the method 500 can be used to design a patient-specific artificial disc implant. Certain aspects of the method 500 are generally similar to certain aspects of the method 400 described previously. Accordingly, the following description of the method 500 focuses on aspects of the method 500 not described with respect to the method 400, with the understanding that the description of similar steps in method 400 applies to like steps in the method 500.

Similar to method 400, the method 500 can begin in step 502 by obtaining patient data. Patient data can include, for example, image data of the patient's spine. In some embodiments, the patient data may also include other patient data and/or data from one or more kinematic studies performed on the patient. The method 500 further includes generating, based at least in part on the image data, a virtual model of one or more regions of the patient's anatomy in step 504. The virtual model can be similar to the virtual model described in detail above in step 404 of method 400. As with method 400, in some embodiments step 504 can be omitted, and the method 500 can proceed from step 502 directly to step 506.

The method 500 can continue in step 506 by analyzing the kinematics of one or more joints in the patient's spine based on the patient data. Analyzing the kinematics of the one or more joints can include using the software module to evaluate one or more kinematic parameters, as described in detail above in step 402 of method 400. In some embodiments, step 506 can be done automatically using the software module, can be partially automated, or can be done manually by manipulating the virtual model generated in step 504. In embodiments in which kinematic data is received along with patient data in step 502, step 506 can optionally be omitted, and the method 500 can continue directly to step 508.

In some embodiments, analyzing the kinematics in step 506 includes comparing the determined kinematic parameter values to one or more kinematic criteria (e.g., the reference kinematic parameter values previously described) associated with the kinematic parameters, as described in detail with respect to step 408 of method 400. If one or more of the determined kinematic parameter values does not meet the corresponding reference kinematic parameter value (and/or is not within a threshold degree of deviation from the corresponding reference kinematic parameter values, such as within 5%, within 10%, within 20%, etc.), the method 500 can provide a notification to a user (e.g., a physician) that the kinematics should be modified/optimized when the patient-specific implant is designed. In some embodiments, and as previously described, the software module may further recommend a secondary procedure (e.g., a decompression procedure, scar tissue removal, etc.) to perform before, during, or after implanting the patient-specific implant to ensure that the kinematics of the patient will be improved following the implant procedure. The predicted outcome of the secondary procedure(s) can be inputted into the software module to determine the modified/optimized patient-specific implant. Accordingly, the patient-specific implant can be modified/optimized for a spine in which the secondary procedure(s) are performed concurrently with or after implantation of the patient-specific implant.

In step 508, a user and/or the software module can determine a target anatomical configuration, as previously described with respect to step 406 of method 400. After the target anatomical configuration has been determined, the method 500 can continue in step 510 by performing a second kinematic analysis to determine the range of motion of the joint under the target anatomical configuration determined in step 508. The second kinematic analysis can be generally similar to the kinematic analysis performed in step 506, and can be done in addition to, or in lieu of, the kinematic analysis in step 506. In some embodiments, the second kinematic analysis can serve as a "check" on the target anatomical configuration. For example, in some embodiments, the second kinematic analysis must show that the kinematics associated with the target anatomical configuration meet one or more predefined kinematic criteria (e.g., specific threshold values and/or ranges for the kinematic parameters that are typical for a "healthy" joint). The predefined kinematic criteria used in step 410 can be the same or different than the kinematic criteria used in step 506. If the kinematic analysis shows that the target anatomical configuration does not achieve the one or more predefined kinematic criteria, such as if the kinematic analysis shows the target anatomical configuration prevents the virtual model from meeting a threshold degree range of motion, the user may be prompted to further manipulate or otherwise adjust the target anatomical configuration using the virtual model (e.g., as done in step 506). After additional manipulation to the target anatomical configuration, the second kinematic analysis can be repeated to confirm that the kinematics associated with the revised target anatomical configuration achieves the one or more predefined kinematic criteria. Once the kinematic criteria are achieved, the method 500 can continue.

The method 500 continues by designing a patient-specific implant in step 512. Designing the patient-specific implant in step 512 can be generally similar to designing the patient-specific implant in step 408 of the method 400. In some embodiments, the patient-specific implant is designed to provide the kinematics determined in step 506 when the patient-specific implant is implanted in the patient. In other embodiments, such as in embodiments in which the kinematics determined in step 506 did not meet the one or more predefined kinematic criteria, the patient-specific implant is designed to provide kinematics in accordance with one or more predefined criteria (e.g., to mimic a "healthy" joint). In some embodiments, a virtual model of the designed patient-specific implant can be generated and combined with the virtual model of the patient's spine to create a combined virtual model showing the patient-specific implant in the patient's spine.

In some embodiments, the method 500 can continue in step 514 by performing a third kinematic analysis. The third kinematic analysis can include evaluating the one or more kinematic parameters of the patient's spine with the patient-specific implant, and comparing the evaluated kinematic parameters to one or more kinematic criteria, which can be the same as or different than the kinematic criteria used in steps 506 and 510. If the evaluated kinematic parameters do not match the one or more criteria, the method 500 can (i) prompt a user to provide further adjustments to the target anatomical configuration, and/or (ii) provide a suggested adjustment to the target anatomical configuration and/or the patient-specific implant. In some embodiments, the method 500 may prevent the patient-specific implant being manufactured until the predefined kinematic criteria are met (e.g., design data for the patient-specific implant can be transmitted to a manufacturing system only after the patient-specific implant is shown to provide the one or more kinematic criteria). Once the third kinematic analysis confirms that the patient-specific implant achieves the kinematic criteria, the patient-specific implant can be manufactured in step 516, which can be generally similar to step 410 of method 400. The manufactured implant can then be delivered to the operating room to be implanted into the patient.

In combination with any of the above methods, the systems and methods described herein can also generate a medical treatment plan for a patient in addition to designing a patient-specific implant. The medical treatment plan can include surgical information, surgical plans, technology recommendations (e.g., device and/or instrument recommendations), in addition to the medical device designs. For example, the medical treatment plan can include at least one treatment procedure (e.g., a surgical procedure or intervention) for implanting the patient-specific implant. The systems described herein can be configured to generate a medical treatment plan for a patient suffering from an orthopedic or spinal disease or disorder, such as trauma (e.g., fractures), cancer, deformity, degeneration, pain (e.g., back pain, leg pain), irregular spinal curvature (e.g., scoliosis, lordosis, kyphosis), irregular spinal displacement (e.g., spondylolisthesis, lateral displacement axial displacement), osteoarthritis, lumbar degenerative disc disease, cervical degenerative disc disease, lumbar spinal stenosis, or cervical spinal stenosis, or a combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disc, a hard disc drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include but are not limited to physically mateable and/or physically interacting components and/or wirelessly interactable and/or wirelessly interacting components and/or logically interacting and/or logically interactable components.

The embodiments, features, systems, devices, materials, methods and techniques described herein may, in some embodiments, be similar to any one or more of the embodiments, features, systems, devices, materials, methods and techniques described in the following:

U.S. application Ser. No. 16/048,167, filed on Jul. 27, 2017, titled "SYSTEMS AND METHODS FOR ASSISTING AND AUGMENTING SURGICAL PROCEDURES;"

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY;"

U.S. application Ser. No. 16/207,116, filed on Dec. 1, 2018, titled "SYSTEMS AND METHODS FOR MULTI-PLANAR ORTHOPEDIC ALIGNMENT;"

U.S. application Ser. No. 16/352,699, filed on Mar. 13, 2019, titled "SYSTEMS AND METHODS FOR ORTHO-PEDIC IMPLANT FIXATION;"

U.S. application Ser. No. 16/383,215, filed on Apr. 12, 2019, titled "SYSTEMS AND METHODS FOR ORTHO-PEDIC IMPLANT FIXATION;"

U.S. application Ser. No. 16/569,494, filed on Sep. 12, 2019, titled "SYSTEMS AND METHODS FOR ORTHO-PEDIC IMPLANTS;"

U.S. application Ser. No. 62/773,127, filed on Nov. 29, 2018, titled "SYSTEMS AND METHODS FOR ORTHO-PEDIC IMPLANTS;"

U.S. application Ser. No. 62/928,909, filed on Oct. 31, 2019, titled "SYSTEMS AND METHODS FOR DESIGN-ING ORTHOPEDIC IMPLANTS BASED ON TISSUE CHARACTERISTICS;" and U.S. application Ser. No. 16/735,222, filed Jan. 6, 2020, titled "PATIENT-SPECIFIC MEDICAL PROCEDURES AND DEVICES, AND ASSOCIATED SYSTEMS AND METHODS."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

We claim:

1. A computer-implemented method for designing a patient-specific implant, the method comprising:
   obtaining patient data, the patient data including:
      image data of one or more regions of a patient's spine, wherein the image data depicts a native anatomical configuration of the one or more regions, and
      kinematic data associated with the one or more regions of a patient's spine, wherein the kinematic data includes values for one or more kinematic parameters;
   determining a target anatomical configuration for the one or more regions, wherein the target anatomical configuration is different than the native anatomical configuration; and
   designing a patient-specific implant based at least in part on the target anatomical configuration and the kinematic parameter values, wherein, when the patient-specific implant is implanted in the patient, the patient-specific implant is configured to provide the target anatomical configuration while maintaining or improving the kinematic parameter values.

2. The method of claim 1 wherein obtaining the kinematic data includes determining the values of the one or more kinematic parameters based on the image data.

3. The method of claim 2 wherein determining the values of the one or more kinematic parameters based on the image data includes analyzing the image data using one or more artificial intelligence architectures.

4. The method of claim 1 wherein obtaining the kinematic data includes receiving the values of the one or more kinematic parameters.

5. The method of claim 1 wherein the one or more kinematic parameters include range of motion, angle of bend, angle of rotation, displacement, flexion, extension, flexion/extension arc, lateral bending, left/right bending arc, and/or axial rotation, and wherein the values for the one or more kinematic parameters include values for range of motion, angle of bend, angle of rotation, displacement, flexion, extension, flexion/extension arc, lateral bending, left/right bending arc, and/or axial rotation.

6. The method of claim 1, further comprising:
   comparing the kinematic parameter values to one or more kinematic criteria; and
   if the kinematic parameter values meet the one or more kinematic criteria, designing the patient-specific implant such that, when the patient-specific implant is implanted in the patient, the patient-specific implant is configured to maintain the kinematic parameter values; and
   if the kinematic parameter values do not meet the one or more kinematic criteria, designing the patient-specific implant such that, when the patient-specific implant is implanted in the patient, the patient-specific implant is configured to improve the kinematic parameter values.

7. The method of claim 6 wherein the kinematic criteria include reference kinematic parameter values.

8. The method of claim 1 wherein the patient-specific implant is configured to fit between a first anatomical structure and a second anatomical structure, and wherein designing the patient-specific implant based on the target anatomical configuration includes:
   analyzing a first topography of the first anatomical structure;
   designing a first endplate of the patient-specific implant to mate with the first topography of the first anatomical structure;
   analyzing a second topography of the second anatomical structure; and
   designing a second endplate of the patient-specific implant to mate with the second topography of the second anatomical endplate.

9. The method of claim 1 wherein the patient-specific implant is an artificial disc having a first endplate, a second endplate, and a core between the first endplate and the second endplate, and wherein designing the patient-specific implant includes:
   designing the first endplate to mate with the topography of a first anatomical structure in the patient's spine;
   designing the second endplate to mate with the topography of a second anatomical structure in the patient's spine; and
   designing the core to maintain or improve the kinematic parameter values when the patient-specific implant is implanted in the patient.

10. The method of claim 9 wherein designing the core includes selecting a combination of one or more elastomeric polymers, one or more rigid polymers, one or more ceramic materials, and/or one or more metallic materials to form the core.

11. The method of claim 1 wherein determining the target anatomical configuration includes:
   generating a virtual model of the native anatomical configuration based on the image data; and
   receiving one or more manipulations to the virtual model to place the virtual model in the target anatomical configuration.

12. The method of claim 1 wherein determining the target anatomical configuration includes:
   identifying one or more reference patient data sets; and
   determining the target anatomical configuration based on the one or more reference patient data sets.

13. The method of claim 1, further comprising generating computer-executable manufacturing instructions, that, when executed, direct a manufacturing system to manufacture the patient-specific implant.

14. The method of claim 13, further comprising transmitting the computer-executable manufacturing instructions to the manufacturing system to manufacture the patient-specific implant.

15. A system for designing a patient-specific implant, the system including:
   one or more processors; and
   a memory storing instructions that, when executed by the one or more processors, cause the system to perform operations comprising:
      obtaining patient data, the patient data including:
         image data of one or more regions of a patient's spine, wherein the image data depicts a native anatomical configuration of the one or more regions, and
         kinematic data associated with the one or more regions of a patient's spine, wherein the kinematic data includes values for one or more kinematic parameters;
      determining a target anatomical configuration for the one or more regions, wherein the target anatomical configuration is different than the native anatomical configuration; and
      designing a patient-specific implant based at least in part on the target anatomical configuration and kinematic parameter values, wherein, when the patient-specific implant is implanted in the patient, the patient-specific implant is configured to provide the target anatomical configuration while maintaining or improving the kinematic parameter values.

16. The system of claim 15 wherein obtaining the kinematic data includes determining the values of the one or more kinematic parameters based on the image data.

17. The system of claim 16 wherein determining the values of the one or more kinematic parameters based on the image data includes analyzing the image data using one or more artificial intelligence architectures.

18. The system of claim 15 wherein obtaining the kinematic data includes receiving the values of the one or more kinematic parameters.

19. The system of claim 15 wherein the one or more kinematic parameters include range of motion, angle of bend, angle of rotation, displacement, flexion, extension, flexion/extension arc, lateral bending, left/right bending arc, and/or axial rotation, and wherein the values for the one or more kinematic parameters include values for range of motion, angle of bend, angle of rotation, displacement, flexion, extension, flexion/extension arc, lateral bending, left/right bending arc, and/or axial rotation.

20. The system of claim 15, the operations further comprising:
   comparing the kinematic parameter values to one or more kinematic criteria; and
   if the kinematic parameter values meet the one or more kinematic criteria, designing the patient-specific implant such that, when the patient-specific implant is implanted in the patient, the patient-specific implant is configured to maintain the kinematic parameter values; and
   if the kinematic parameter values do not meet the one or more kinematic criteria, designing the patient-specific implant such that, when the patient-specific implant is implanted in the patient, the patient-specific implant is configured to improve the kinematic parameter values.

21. The system of claim 20 wherein the kinematic criteria include reference kinematic parameter values.

22. The system of claim 15 wherein the patient-specific implant is an artificial disc having a first endplate, a second endplate, and a core between the first endplate and the second endplate, and wherein the operation of designing the patient-specific implant includes:
   designing the first endplate to mate with the topography of a first anatomical structure in the patient's spine;
   designing the second endplate to mate with the topography of a second anatomical structure in the patient's spine; and
   designing the core to maintain or improve the kinematic parameter values when the patient-specific implant is implanted in the patient.

23. The system of claim 15 wherein determining the target anatomical configuration includes:
   identifying one or more reference patient data sets; and
   determining the target anatomical configuration based on the one or more reference patient data sets.

24. The system of claim 15, the operations further comprising generating manufacturing data associated with the patient-specific implant, wherein the manufacturing data is configured to direct a manufacturing system to manufacture the patient-specific implant.

25. A non-transitory computer-readable storage medium storing instructions that, when executed by a computing system, cause the computing system to perform operations comprising:
   obtaining patient data, the patient data including:
      image data of one or more regions of a patient's spine, wherein the image data depicts a native anatomical configuration of the one or more regions, and
      kinematic data associated with the one or more regions of the patient's spine, wherein the kinematic data includes values for one or more kinematic parameters;
   determining a target anatomical configuration for the one or more regions, wherein the target anatomical configuration is different than the native anatomical configuration; and
   designing a patient-specific implant based at least in part on the target anatomical configuration and the kinematic parameter values, wherein, when the patient-specific implant is implanted in the patient, the patient-specific implant is configured to provide the target anatomical configuration while maintaining or improving the kinematic parameter values.

26. The non-transitory computer-readable storage medium of claim 25 wherein the patient-specific implant is an artificial disc having a first endplate, a second endplate, and a core between the first endplate and the second endplate, and wherein the operation of designing the patient-specific implant includes:
   designing the first endplate to mate with the topography of a first anatomical structure in the patient's spine;
   designing the second endplate to mate with the topography of a second anatomical structure in the patient's spine; and designing the core to provide the kinematic parameter values when the patient-specific implant is implanted in the patient.

27. The non-transitory computer-readable storage medium of claim 25 obtaining the kinematic data includes using one or more artificial intelligence architectures to determine the values of the one or more kinematic parameters based on the image data.

28. The non-transitory computer-readable storage medium of claim 25 wherein the one or more kinematic parameters include range of motion, angle of bend, angle of rotation, displacement, flexion, extension, flexion/extension arc, lateral bending, left/right bending arc, and/or axial rotation, and wherein the values for the one or more kinematic parameters include values for range of motion, angle of bend, angle of rotation, displacement, flexion, extension, flexion/extension arc, lateral bending, left/right bending arc, and/or axial rotation.

29. The non-transitory computer-readable storage medium of claim 25 wherein the operations further comprise:
   comparing the kinematic parameter values to one or more kinematic criteria; and
   if the kinematic parameter values meet the one or more kinematic criteria, designing the patient-specific implant such that, when the patient-specific implant is implanted in the patient, the patient-specific implant is configured to maintain the kinematic parameter values; and
   if the kinematic parameter values do not meet the one or more kinematic criteria, designing the patient-specific implant such that, when the patient-specific implant is implanted in the patient, the patient-specific implant is configured to improve the kinematic parameter values.

30. The non-transitory computer-readable storage medium of claim 29 wherein the kinematic criteria include reference kinematic parameter values.

31. The non-transitory computer-readable storage medium of claim 25 wherein the operations further comprise generating manufacturing data associated with the patient-specific implant, wherein the manufacturing data is configured to direct a manufacturing system to manufacture the patient-specific implant.

32. A computer-implemented method for designing a patient-specific implant, the method comprising:
   obtaining patient data, the patient data including image data of one or more regions of a patient's spine, wherein the image data depicts a native anatomical configuration of the one or more regions;
   determining a target anatomical configuration for the one or more regions, wherein the target anatomical configuration is different than the native anatomical configuration;
   predicting kinematic data based on the target anatomical configuration, the kinematic data being associated with the one or more regions of the patient's spine, wherein the kinematic data includes predicted kinematic parameter values for one or more kinematic parameters; and
   designing a patient-specific implant based at least in part on the target anatomical configuration and the predicted kinematic parameter values, wherein, when the patient-specific implant is implanted in the patient, the patient-specific implant is configured to provide the target anatomical configuration and the predicted kinematic parameter values.

33. The method of claim 32 wherein predicting the kinematic data includes determining the values of the one or more kinematic parameters based on the image data.

34. The method of claim 32, further comprising:
   comparing the predicted kinematic parameter values to one or more kinematic criteria; and
   in response to the predicted kinematic parameter values meeting the one or more kinematic criteria, designing the patient-specific implant such that, when the patient-specific implant is implanted in the patient, the patient-specific implant is configured to maintain the predicted kinematic parameter values; and
   in response to the predicted kinematic parameter values not meeting the one or more kinematic criteria, designing the patient-specific implant such that, when the patient-specific implant is implanted in the patient, the patient-specific implant is configured to improve the predicted kinematic parameter values.

35. A system for designing a patient-specific implant, the system including:
   one or more processors; and
   a memory storing instructions that, when executed by the one or more processors, cause the system to perform operations comprising:
      obtaining patient data, the patient data including:
         image data of one or more regions of a patient's spine, wherein the image data depicts a native anatomical configuration of the one or more regions;
      determining a target anatomical configuration for the one or more regions, wherein the target anatomical configuration is different than the native anatomical configuration;
      predicting kinematic data based on the target anatomical configuration, the kinematic data being associated with the one or more regions of the patient's spine, wherein the kinematic data includes predicted kinematic parameter values for one or more kinematic parameters; and
      designing a patient-specific implant based at least in part on the target anatomical configuration and the predicted kinematic parameter values, wherein, when the patient-specific implant is implanted in the patient, the patient-specific implant is configured to provide the target anatomical configuration and the predicted kinematic parameter values.

36. The system of claim 35 wherein the patient-specific implant is an artificial disc having a first endplate, a second endplate, and a core between the first endplate and the second endplate, and wherein the operation of designing the patient-specific implant includes:
   designing the first endplate to mate with the topography of a first anatomical structure in the patient's spine;
   designing the second endplate to mate with the topography of a second anatomical structure in the patient's spine; and
   designing the core to maintain or improve the predicted kinematic parameter values when the patient-specific implant is implanted in the patient.

37. The system of claim 35 wherein determining the target anatomical configuration includes:
   identifying one or more reference patient data sets; and
   determining the target anatomical configuration based on the one or more reference patient data sets.

38. A non-transitory computer-readable storage medium storing instructions that, when executed by a computing system, cause the computing system to perform operations comprising:
- obtaining patient data, the patient data including image data of one or more regions of a patient's spine, wherein the image data depicts a native anatomical configuration of the one or more regions;
- determining a target anatomical configuration for the one or more regions, wherein the target anatomical configuration is different than the native anatomical configuration;
- predicting kinematic data based on the target anatomical configuration, the kinematic data being associated with the one or more regions of the patient's spine, wherein the kinematic data includes predicted kinematic parameter values for one or more kinematic parameters; and
- designing a patient-specific implant based at least in part on the target anatomical configuration and the predicted kinematic parameter values, wherein, when the patient-specific implant is implanted in the patient, the patient-specific implant is configured to provide the target anatomical configuration and the predicted kinematic parameter values.

39. The non-transitory computer-readable storage medium of claim 38 wherein the operation of predicting the kinematic data includes using one or more artificial intelligence architectures to determine the predicted values of the one or more kinematic parameters based on the image data.

40. The non-transitory computer-readable storage medium of claim 38 wherein the operations further comprise generating manufacturing data associated with the patient-specific implant, wherein the manufacturing data is configured to direct a manufacturing system to manufacture the patient-specific implant.

* * * * *